United States Patent
Iwase et al.

(10) Patent No.: US 9,700,210 B2
(45) Date of Patent: Jul. 11, 2017

(54) IMAGE PROCESSING APPARATUS AND METHOD FOR CONTROLLING THE SAME

(75) Inventors: Yoshihiko Iwase, Yokohama (JP); Shinji Uchiyama, Yokohama (JP); Kiyohide Satoh, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 803 days.

(21) Appl. No.: 12/714,798

(22) Filed: Mar. 1, 2010

(65) Prior Publication Data

US 2010/0220914 A1     Sep. 2, 2010

(30) Foreign Application Priority Data

Mar. 2, 2009 (JP) ................................ 2009-048514
Mar. 2, 2009 (JP) ................................ 2009-048520

(51) Int. Cl.
G06K 9/00 (2006.01)
A61B 5/00 (2006.01)
G06T 7/00 (2017.01)

(52) U.S. Cl.
CPC .......... *A61B 5/0066* (2013.01); *A61B 5/0073* (2013.01); *G06T 7/0012* (2013.01); *G06K 2209/05* (2013.01); *G06T 2207/10072* (2013.01); *G06T 2207/30041* (2013.01)

(58) Field of Classification Search
CPC ...... A61B 3/102; G06F 19/321; G06T 7/0012
USPC .................................................. 382/128–134
See application file for complete search history.

(56) References Cited

U.S. PATENT DOCUMENTS

| | | | | |
|---|---|---|---|---|
| 5,861,955 | A | * 1/1999 | Gordon | ................. A61B 3/107 356/511 |
| 5,881,124 | A | * 3/1999 | Giger | .................... G06T 7/0012 250/363.04 |
| 2006/0077395 | A1 | * 4/2006 | Chan et al. | ................... 356/497 |
| 2007/0103693 | A1 | * 5/2007 | Everett | ................... G06T 19/00 356/479 |
| 2007/0285619 | A1 | 12/2007 | Aoki et al. | |
| 2008/0232542 | A1 | * 9/2008 | Lin | ............................. 378/16 |

FOREIGN PATENT DOCUMENTS

| | | |
|---|---|---|
| JP | 2007-325831 A | 12/2007 |
| JP | 2008-073099 A | 4/2008 |
| JP | 2009507537 A | 2/2009 |

* cited by examiner

*Primary Examiner* — Elaine Gort
*Assistant Examiner* — Rajiv Raj
(74) *Attorney, Agent, or Firm* — Canon USA Inc., IP Division

(57) ABSTRACT

An image processing apparatus includes an image acquisition unit configured to acquire a tomographic image of an object, a layer detection unit configured to detect a layer that constitutes the object from the tomographic image acquired by the image acquisition unit, and a normal structure estimation unit configured to estimate a normal structure of the layer based on the layer detected by the layer detection unit and a feature that is modified by a lesion of the layer.

57 Claims, 22 Drawing Sheets

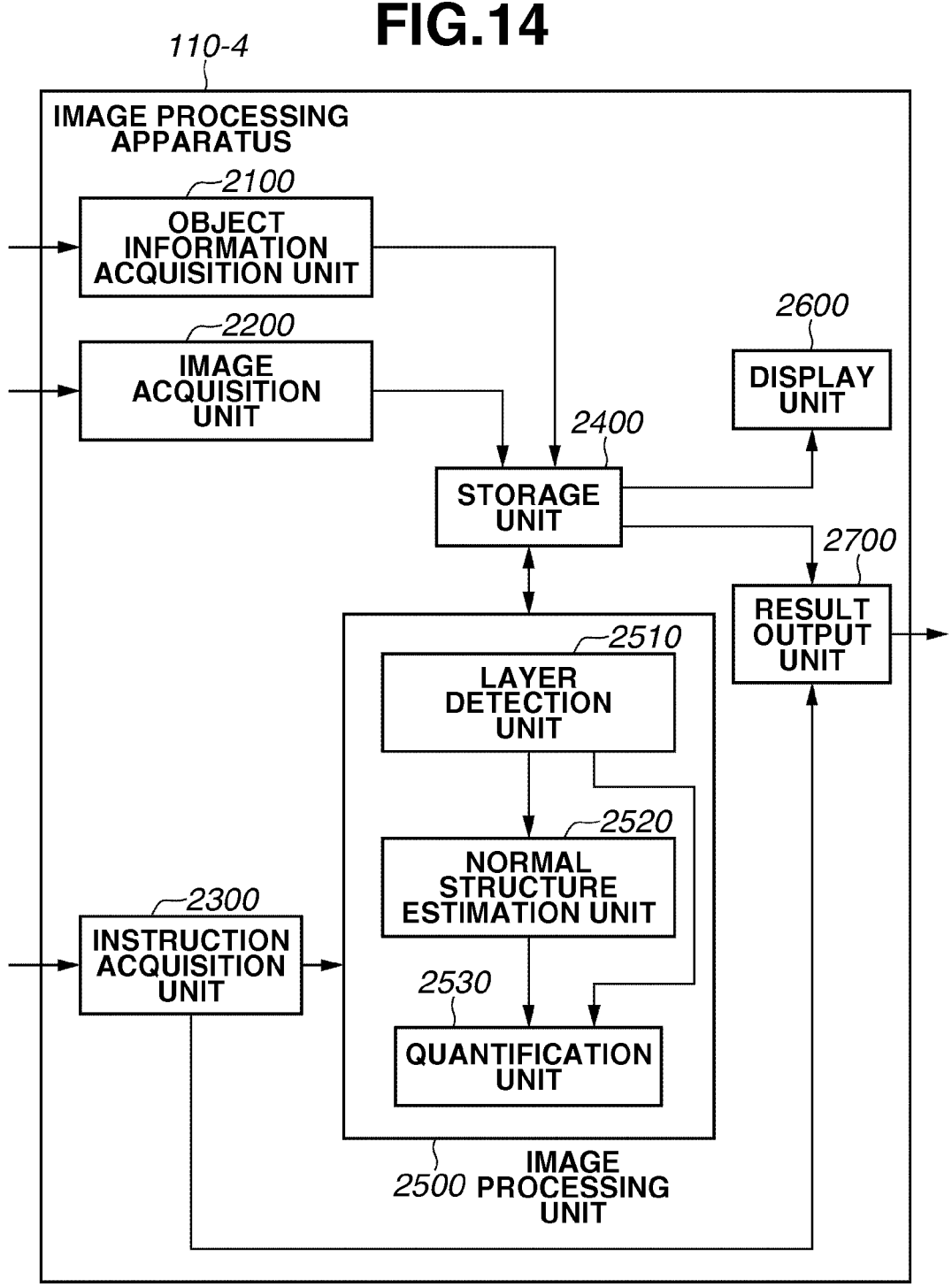

*1400a*

*1400b*

*1401*

*1402*

IMAGE PROCESSING APPARATUS AND METHOD FOR CONTROLLING THE SAME

BACKGROUND OF THE INVENTION

Field of the Invention

The present invention relates to an image processing system for processing a tomographic image of an object.

Description of the Related Art

To diagnose lifestyle related diseases and other various diseases, which may lead to blindness, in their early stages, inspections are conventionally performed based on captured images of eye portions (i.e., objects). For example, a tomographic image acquiring apparatus using an Optical Coherence Tomography (hereinafter, referred to as "OCT") can be used to observe a three-dimensional state of an internal retinal layer of an eye portion. Therefore, the tomographic image acquiring apparatus is expected to be a prospective diagnosis apparatus that can accurately diagnose various diseases.

In a cross-sectional layer image (i.e., a tomographic image) of an eye portion obtained using the OCT, the stage of a disease (e.g., glaucoma, age-related macular degeneration, and macular edema) and the degree of recovery from the disease after treatment can be quantitatively diagnosed by measuring the thickness of each layer (e.g., a nerve fiber layer) that constitutes the retina in the eye portion or the thickness of the entire retinal layer.

Conventionally, to measure the thickness of each layer, it was necessary for a physician or an engineer to manually designate a boundary of each layer of the retina on a two-dimensional tomographic image (i.e., a B-scan image), which can be obtained by clipping a target cross section from a three-dimensionally captured tomographic image. Further, to obtain a three-dimensional distribution with respect to the thickness of each layer, it was necessary to presume a three-dimensional tomographic image as an assembly of two-dimensional tomographic images and designate a boundary of a target layer on each two-dimensional tomographic image.

However, the work for manually designating the boundary of the target layer is not easy for an operator (e.g., a physician or an engineer). Further, the work for manually designating the boundary of the target layer tends to generate a dispersion that results from differences of individual operators as well as differences in work date and time. Therefore, performing quantification at an expected accuracy level was difficult. As discussed in Japanese Patent Application Laid-Open No. 2008-73099 and Japanese Patent Application Laid-Open No. 2007-325831, for the purpose of reducing the operator's burden and eliminating the dispersion in the work, there is a conventional technique for causing a computer to detect a boundary of each layer of the retina from a tomographic image and measuring the thickness of each layer.

Further, the age-related macular degeneration or a similar disease is characteristic in that the shape of a retinal pigment epithelium changes into a wavy shape according to the condition of a disease. Therefore, it is effective to quantify the degree of its deformation to identify the condition of the disease.

FIGS. 20A to 20C are schematic views illustrating examples of the layer structure of a general retina. FIG. 20A illustrates an example of a retinal layer structure of a normal eye. FIG. 20B illustrates an example of a retinal layer structure that has changed due to the age-related macular degeneration. A retinal pigment epithelium 1400a of the normal eye illustrated in FIG. 20A includes a smooth curve that represents a boundary structure. On the other hand, a retinal pigment epithelium 1400b having been modified by the age-related macular degeneration illustrated in FIG. 20B has a portion whose shape has partly changed into a wavy shape. As described above, the tomographic image of an eye portion obtained using the OCT is a three-dimensional image. However, to simplify the following description, FIGS. 20A to 20C illustrate two-dimensional images that can be obtained by cutting the three-dimensional image along a plane. Further, since the retinal pigment epithelium is a thin layer, it is indicated by a single line in FIGS. 20A to 20C.

In the following description, a boundary between the retinal pigment epithelium and its upper or lower layer is referred to as a "boundary of the retinal pigment epithelium", or is simply referred to as a "layer boundary." Further, an estimated boundary position that represents a layer boundary in a normal state (i.e., in a non-diseased state) is referred to as a "normal structure of the boundary of the retinal pigment epithelium", or is simply referred to as a "normal structure." Further, an example of the age-related macular degeneration diagnosing method using the OCT includes obtaining an actual boundary (indicated by 1401 in FIG. 20C) of the retinal pigment epithelium based on the image illustrated in FIG. 20B, as a boundary actually observable on the tomographic image, and further obtaining its normal structure (indicated by 1402 in FIG. 20C) on the same tomographic image. The diagnosing method further includes quantifying the state of the disease according to an area (or a volume) that represents a difference (a hatched portion illustrated in FIG. 20C) between the actual boundary (1401) of the retinal pigment epithelium that is observable on the tomographic image and its normal structure (1402) on the same tomographic image.

However, the above-described work is conventionally performed based on a manual work by a physician or an engineer. It is therefore desired to reduce the operator's burden and eliminate the resulting dispersion. In this respect, it is expected to automatically detect the boundary of the retinal pigment epithelium from the tomographic image and estimate its normal structure.

The above-described detection of the boundary of the retinal pigment epithelium can be performed using a technique discussed in Japanese Patent Application Laid-Open No. 2008-73099 or in Japanese Patent Application Laid-Open No. 2007-325831. On the other hand, because the above-described normal structure cannot be observed as image features on the tomographic image, the normal structure cannot be estimated using the technique discussed in Japanese Patent Application Laid-Open No. 2008-73099 or in Japanese Patent Application Laid-Open No. 2007-325831. Hence, it is usual that an elliptic curve applied to a boundary of the retinal pigment epithelium detected from a two-dimensional tomographic image (i.e., B-scan image) so as to minimize square errors is regarded as its normal structure.

FIGS. 21A to 21D are schematic views illustrating examples of a layer structure of an eye portion that has been captured using the OCT.

More specifically, the layer structures illustrated in FIGS. 21A to 21D are examples including a macula lutea portion of the retina. In general, the tomographic image of an eye portion obtained using the OCT is a three-dimensional image. However, to simplify the following description, FIGS. 21A to 21D illustrate two-dimensional images that can be obtained by cutting the three-dimensional image along a plane.

As illustrated in FIGS. 21A to 21D, a retinal pigment epithelium 1001, a nerve fiber layer 1002, and an inner limiting membrane 1003 can be observed as individually discriminable layers. For example, in a case where a tomographic image illustrated in FIG. 21A is input, the stage of a disease (e.g., glaucoma) or the degree of recovery from the disease after treatment can be quantitatively diagnosed by measuring a thickness (indicated by T1 in FIG. 21A) of the nerve fiber layer 1002 or a thickness (indicated by T2 in FIG. 21A) of the entire retinal layer.

To measure the thickness of each layer, it was conventionally necessary for a physician or an engineer to manually designate a boundary of each layer of the retina on a two-dimensional tomographic image (i.e., a B-scan image), which can be obtained by clipping a target cross section from a three-dimensionally captured tomographic image. For example, to check the thickness (T1) of the nerve fiber layer 1002 illustrated in FIG. 21A, it was necessary to designate the inner limiting membrane 1003 and a lower boundary 1004 of the nerve fiber layer (i.e., a boundary between the nerve fiber layer 1002 and a layer positioned beneath the nerve fiber layer 1002) on the tomographic image, as understood from FIG. 21B. Further, to check the thickness (indicated by T2 in FIG. 21A) of the entire retinal layer, it was further necessary to designate a boundary 1005 of the retinal pigment epithelium 1001 (i.e., a boundary between the retinal pigment epithelium 1001 and a layer positioned beneath the retinal pigment epithelium 1001).

Further, to obtain a three-dimensional distribution with respect to the thickness of each layer, it was necessary to designate a boundary of a target layer on each two-dimensional tomographic image based on the assumption that a three-dimensional tomographic image is an assembly of a plurality of two-dimensional tomographic images.

However, the work for manually designating a layer boundary is not easy for an operator (e.g., a physician or an engineer). Further, the work for manually designating the boundary of the target layer tends to generate a dispersion that results from differences of individual operators as well as differences in work date and time. Therefore, performing quantification at an expected accuracy level was difficult.

As discussed in Japanese Patent Application Laid-Open No. 2008-73099 and Japanese Patent Application Laid-Open No. 2007-325831, for the purpose of reducing the operator's burden and eliminating the dispersion in the work, there is a conventional technique for causing a computer to detect a boundary of each layer of the retina from a tomographic image and measuring the thickness of each layer.

Further, the age-related macular degeneration or a similar disease is characteristic in that the shape of the retinal pigment epithelium changes into a wavy shape according to the condition of a disease. Therefore, it is effective to quantify the degree of its deformation to identify the condition of the disease.

FIG. 21A illustrates an example of a retinal layer structure of a normal eye. FIG. 21C illustrates an example of a retinal layer structure that has changed due to the age-related macular degeneration. A retinal pigment epithelium 1001 of the normal eye illustrated in FIG. 21A includes a smooth curve that represents a boundary structure. On the other hand, a retinal pigment epithelium 1001 having been modified by the age-related macular degeneration illustrated in FIG. 21C has a portion whose shape has partly changed into a wavy shape.

In the following description, an estimated boundary position that represents a layer boundary in a normal state (i.e., in a non-diseased state) is referred to as a "normal structure of the boundary of the retinal pigment epithelium", or is simply referred to as a "normal structure." Further, an example of the age-related macular degeneration diagnosing method using the OCT includes obtaining an actual boundary (actual measurement data indicated by a solid line 1005 in FIG. 20D) of the retinal pigment epithelium, as a boundary actually observable on the tomographic image, and further obtaining its normal structure (estimation data indicated by a dotted line 1006 in FIG. 21D) on the same tomographic image. The diagnosing method further includes quantifying the state of the disease according to an area (or an overall volume) in each cross section that represents a difference (a hatched portion illustrated in FIG. 21D) between the actual boundary (1005) of the retinal pigment epithelium that is observable on the tomographic image and its normal structure (1006) on the same tomographic image.

However, the above-described work is conventionally performed based on a manual work by a physician or an engineer. It is therefore desired to reduce the operator's burden and eliminate the resulting dispersion. In this respect, it is expected to automatically detect the boundary of the retinal pigment epithelium from the tomographic image and estimate its normal structure.

The above-described detection of the boundary of the retinal pigment epithelium can be performed using the technique discussed in Japanese Patent Application Laid-Open No. 2008-73099 or in Japanese Patent Application Laid-Open No. 2007-325831. On the other hand, because the above-described normal structure cannot be observed as image features on the tomographic image, the normal structure cannot be estimated using the technique discussed in the above-described patent literatures. Hence, it is usual that an elliptic curve applied to a boundary of the retinal pigment epithelium detected from a two-dimensional tomographic image (i.e., B-scan image) so as to minimize square errors is regarded as its normal structure.

The retinal pigment epithelium 1001 is a very thin layer. Therefore, in general, the boundary 1005 of the retinal pigment epithelium may be referred to as "retinal pigment epithelium itself." Therefore, in the following description, the "boundary of the retinal pigment epithelium" can be regarded as being equivalent to the "retinal pigment epithelium itself." Similarly, the "normal structure of the boundary of the retinal pigment epithelium" can be regarded as being equivalent to the "normal structure of the retinal pigment epithelium itself."

However, the above-described normal structure having been estimated by applying an elliptic curve according to the conventional least squares method tends to be greatly different from the actual normal structure. Therefore, even if an area is obtainable as a difference between the normal structure and a detected layer boundary, the obtained area cannot be used as a reliable index that can quantify the state of a disease. Further, if a blood vessel or a facula is included in the tomographic image, the boundary 1005 of the retinal pigment epithelium may not be clearly observed at a portion where the boundary 1005 is overlapped with the blood vessel or the facula. Namely, acquiring the image features of the boundary 1005 of the retinal pigment epithelium may partly fail due to the influence of such an obstacle.

SUMMARY OF THE INVENTION

The present invention is directed to a mechanism that can accurately estimate a normal structure of a layer that constitutes an object.

According to an aspect of the present invention, an image processing apparatus includes an image acquisition unit configured to acquire a tomographic image of an object, a layer detection unit configured to detect a layer that constitutes the object from the tomographic image, and an estimation unit configured to estimate a normal structure of the layer based on the layer detected by the layer detection unit and a feature that is modified by a lesion of the layer.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 14 is a schematic view illustrating an example of a functional configuration of an image processing apparatus according to a fourth exemplary embodiment of the present invention.

DESCRIPTION OF THE EMBODIMENTS

Various exemplary embodiments, features, and aspects of the invention will be described in detail below with reference to the drawings. Exemplary embodiments described below are mere examples and the present invention is not limited to each illustrated configuration.

Figure 1:
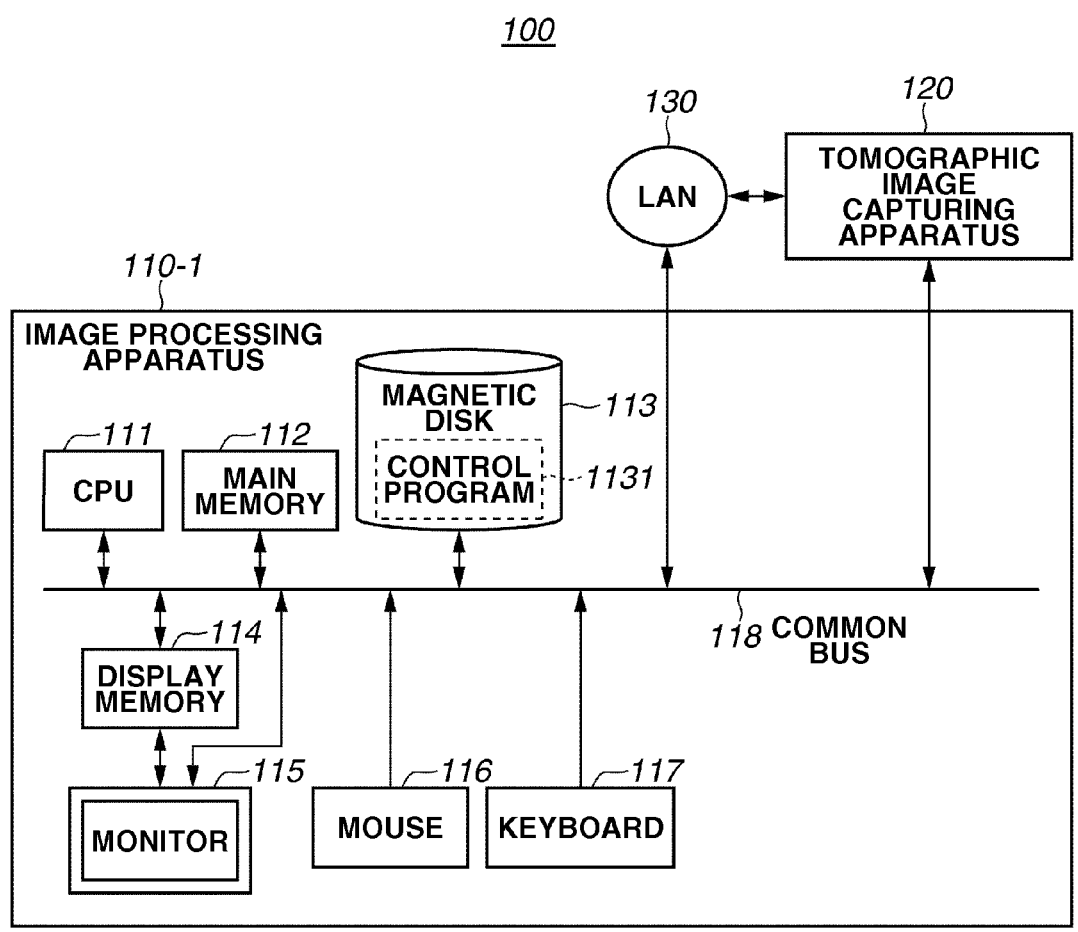
FIG. 1 is a schematic view illustrating an example of a schematic configuration (hardware configuration) of an image processing system according to a first exemplary embodiment of the present invention.

A first exemplary embodiment of the present invention is described below. FIG. 1 is a schematic view illustrating an example of a schematic configuration (i.e., a hardware configuration) of an image processing system 100 according to the first exemplary embodiment of the present invention.

As illustrated in FIG. 1, the image processing system 100 according to the present exemplary embodiment includes an image processing apparatus 110, a tomographic image capturing apparatus 120, and a local area network (LAN) 130. In the following description, the image processing apparatus 110 illustrated in FIG. 1 is referred to as an "image processing apparatus 110-1." More specifically, the image processing system 100 illustrated in FIG. 1 includes the image processing apparatus 110-1 that is connected via the LAN 130 to the tomographic image capturing apparatus 120.

The image processing apparatus 110-1 according to the present exemplary embodiment, for example, detects a layer boundary, such as a boundary of a retinal pigment epithelium that constitutes an eye portion, from a tomographic image of an object (eye portion in the present exemplary embodiment) captured by the tomographic image capturing apparatus 120. The image processing apparatus 110-1, for example, estimates a normal structure of the retinal pigment epithelium based on characteristics such that the shape of the layer changes into a wavy shape due to a disease, such as age-related macular degeneration. The image processing apparatus 110-1 further performs quantification of the disease. In the present exemplary embodiment, an eye portion is an example of the object to be inspected. However, the present invention is not limited to the example described in the present exemplary embodiment and is applicable to any other object that can be captured as a tomographic image.

The image processing apparatus 110-1, as illustrated in FIG. 1, includes a central processing unit (CPU) 111, a main memory 112, a magnetic disk 113, a display memory 114, a monitor 115, a mouse 116, a keyboard 117, and a common bus 118. A control program 1131 is stored in the magnetic disk 113.

The CPU 111 mainly performs an integrated control for the image processing apparatus 110-1 by controlling operations of respective constituent components of the image processing apparatus 110-1. The main memory 112 can store the control program 1131 if it is loaded from the magnetic disk 113, for example, when the CPU 111 executes processing. The main memory 112 can serve as a work area when the CPU 111 executes the control program 1131.

The magnetic disk 113 can memorize (store) an operating system (OS), a device driver for a peripheral device, and the control program 1131. Further, if necessary, the magnetic disk 113 can store various information and data to be used when the CPU 111 executes processing according to the control program 1131, and further store various information and data if obtained through the processing performed by the CPU 111 according to the control program 1131. In the present exemplary embodiment, the CPU 111 executes an integrated control for various operations to be performed by the image processing apparatus 110-1 by executing the control program 1131 stored in the magnetic disk 113.

The display memory 114 temporarily stores data to be displayed on the monitor 115.

The monitor 115 is, for example, constituted by a cathode ray tube (CRT) monitor or a liquid crystal display (LCD) monitor. The monitor 115 displays an image based on the data to be displayed stored in the display memory 114 according to a control signal supplied from the CPU 111.

The mouse 116 and the keyboard 117 are devices that enable users to perform pointing input and character input.

The common bus 118 connects the constituent components provided in the image processing apparatus 110-1 so that these components can communicate with each other. The common bus 118 further connects the internal constituent components of the image processing apparatus 110-1 to the LAN 130 and to the tomographic image capturing apparatus 120 so that each internal constituent component can communicate with an external device via the LAN 130 or can directly communicate with the tomographic image capturing apparatus 120.

The tomographic image capturing apparatus 120 is, for example, an apparatus that can capture a tomographic image of the eye portion. For example, a time domain type OCT or a Fourier domain type OCT can be used for the tomographic image capturing apparatus 120. The tomographic image capturing apparatus 120 can capture a three-dimensional tomographic image of an eye portion of a subject (i.e., a patient) according to an operation of a user (e.g., an engineer or a physician), (not illustrated). Further, the tomographic image capturing apparatus 120 can output an obtained tomographic image to the image processing apparatus 110-1.

The LAN 130 connects, if necessary, the image processing apparatus 110-1 to the tomographic image capturing apparatus 120 so that they can communicate with each other.

The LAN 130 is, for example, constituted by Ethernet®. Alternatively, the connection between the image processing apparatus 110-1 and the tomographic image capturing apparatus 120 can be realized, for example, by using an appropriate interface (e.g., USB and IEEE1394) that can directly connect two apparatuses, instead of using the LAN 130.

Figure 2:
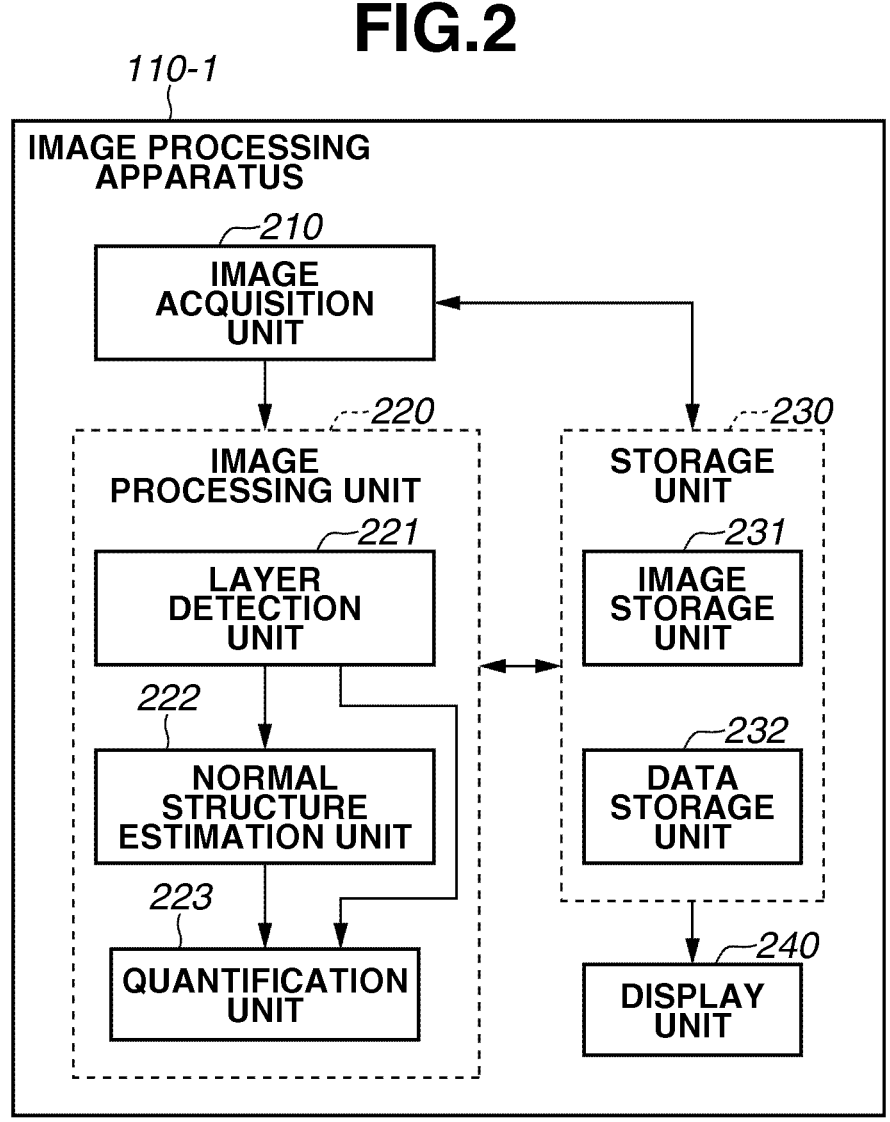
FIG. 2 is a schematic view illustrating an example of a functional configuration of an image processing apparatus according to the first exemplary embodiment of the present invention.

Next, a functional configuration of the image processing apparatus 110-1 illustrated in FIG. 1 is described below in detail. FIG. 2 is a schematic view illustrating an example of the functional configuration of the image processing apparatus 110-1 according to the first exemplary embodiment of the present invention.

As illustrated in FIG. 2, the image processing apparatus 110-1 includes an image acquisition unit 210, an image processing unit 220, a storage unit 230, and a display unit 240, as constituent components that constitute the functional configuration.

In the present exemplary embodiment, for example, the CPU 111 illustrated in FIG. 1 can realize the image acquisition unit 210 and the image processing unit 220 illustrated in FIG. 2 by executing the control program 1131 stored in the magnetic disk 113. Further, for example, the CPU 111 and the control program 1131 in addition to the main memory 112, the magnetic disk 113, or the display memory 114 illustrated in FIG. 1 can cooperatively realize the storage unit 230 illustrated in FIG. 2. Moreover, for example, the CPU 111 and the control program 1131, and the monitor 115 illustrated in FIG. 1 can cooperatively realize the display unit 240.

The image acquisition unit 210 can perform processing for requesting the tomographic image capturing apparatus 120 to transmit a tomographic image of the eye portion (i.e. the object) and acquiring the tomographic image of the eye portion received from the tomographic image capturing apparatus 120. Then, the image acquisition unit 210 sends the acquired tomographic image to the image processing unit 220 and the storage unit 230.

The image processing unit 220 processes the tomographic image sent from the image acquisition unit 210. As illustrated in FIG. 2, the image processing unit 220 includes a layer detection unit 221, a normal structure estimation unit 222, and a quantification unit 223. In the present exemplary embodiment, an example of image processing to be performed by the image processing unit 220 is described below with reference to FIG. 3.

Figure 3:
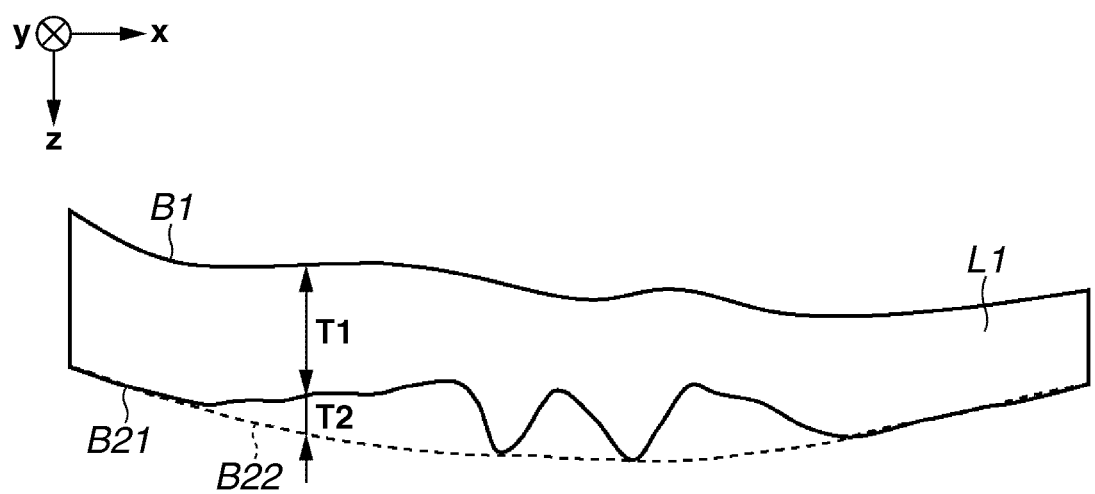
FIG. 3 is a schematic view illustrating an example of a tomographic image input by an image processing unit illustrated in FIG. 2.

FIG. 3 is a schematic view illustrating an example of the tomographic image that can be input to the image processing unit 220 illustrated in FIG. 2. More specifically, similar to FIGS. 20A to 20C, FIG. 3 illustrates an example of a layer structure of the retina in an eye portion. In the following description, a positive direction of the z-coordinate is identical to an eyeground depth direction and an x-y plane is defined by directions perpendicular to the z-coordinate.

The layer detection unit 221 can detect, from an input tomographic image, a layer boundary (indicated by B1 in FIG. 3) of an inner limiting membrane that constitutes an eye portion and a layer boundary of a retinal pigment epithelium (indicated by B21 in FIG. 3), respectively. The content of example processing to be performed by the layer detection unit 221 is described below.

The normal structure estimation unit 222 can perform processing for estimating a normal structure (indicated by B22 in FIG. 3) of the layer based on the layer boundary of the retinal pigment epithelium (indicated by B21 in FIG. 3) detected by the layer detection unit 221 and features modified by a lesion of the retinal pigment epithelium. In FIG. 3, a solid line indicates the boundary (B1 and B21) of the layer detected by the layer detection unit 221. A dotted line indicates the boundary (B21) of the layer estimated by the normal structure estimation unit 222. The content of example processing to be performed by the normal structure estimation unit 222 is described below.

The quantification unit 223 can perform processing for calculating a layer thickness T1 of a layer L1 as well as an area and a volume thereof, based on a detection result obtained by the layer detection unit 221. Further, the quantification unit 223 can quantify a state of the retinal pigment epithelium (more specifically, a turbulence of the retinal pigment epithelium) based on the boundary of the retinal pigment epithelium (indicated by B21 in FIG. 3) detected by the layer detection unit 221 and the normal structure (indicated by B22 in FIG. 3) estimated by the normal structure estimation unit 222. The content of example processing to be performed by the quantification unit 223 is described below in detail.

Next, the storage unit 230 illustrated in FIG. 2 is described below in detail. The storage unit 230, as illustrated in FIG. 2, includes an image storage unit 231 and a data storage unit 232.

The image storage unit 231 stores the tomographic image acquired by the image acquisition unit 210 (and, if necessary, a tomographic image having been processed by the image processing unit 220).

The data storage unit 232 stores function and parameter data that can be used by the image processing unit 220. More specifically, the data storage unit 232 stores mathematical functions to be used when the normal structure estimation unit 222 estimates the normal structure of the retinal pigment epithelium and various parameter data to be used when the layer detection unit 221 obtains the boundary of a layer from the tomographic image.

Further, the data storage unit 232 associates various tomographic images stored in the image storage unit 231 with information relating to the result of various processing performed by the image processing unit 220, and stores the associated data as patient data. In the present exemplary embodiment, the storage unit 230 is, for example, constituted by the magnetic disk 113. Therefore, various tomographic images and the information relating to the result of various processing performed by the image processing unit 220 can be stored in the magnetic disk 113, while they are associated with each other.

More specifically, the storage unit 230 stores tomographic image data acquired by the image acquisition unit 210, layer boundary data detected by the layer detection unit 221, normal structure data estimated by the normal structure estimation unit 222, and numerical data quantified by the quantification unit 223, while associating these data with each other. Further, various data stored in the storage unit 230 (the data storage unit 232) can be also stored in an external server (not illustrated) that is accessible via the LAN 130. In this case, various data stored in the storage unit 230 are transmitted to the external server.

Next, the display unit 240 is described below in detail. The display unit 240 can display the tomographic image obtained by the image acquisition unit 210, the boundary of a layer obtained by the layer detection unit 221 and the normal structure estimation unit 222, and various quantification results quantified by the quantification unit 223.

Figure 4:
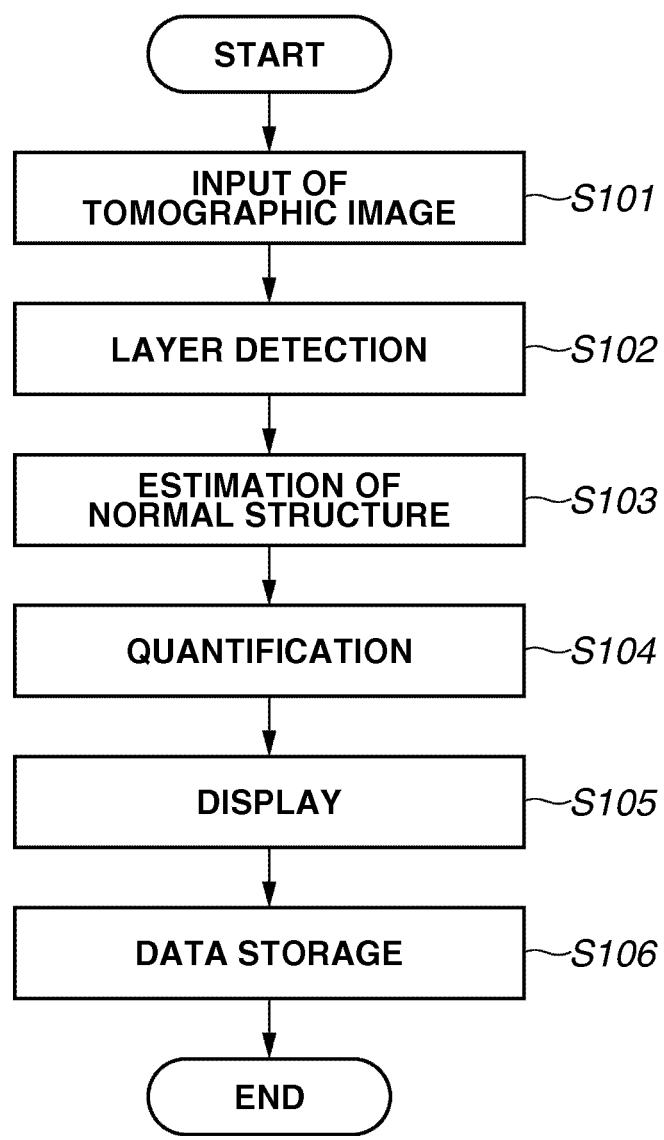
FIG. 4 is a flowchart illustrating an example of a processing procedure of a method for controlling an image processing apparatus according to the first exemplary embodiment of the present invention.

Next, an example procedure of processing to be executed by the image processing apparatus 110-1 according to the present exemplary embodiment is described below with reference to FIG. 4. FIG. 4 is a flowchart illustrating an example of a processing procedure of a method for controlling the image processing apparatus 110-1 according to the first exemplary embodiment of the present invention.

First, in step S101, the image acquisition unit 210 requests the tomographic image capturing apparatus 120 to transmit a tomographic image of an eye portion (i.e., an object), and acquires the tomographic image of the eye portion transmitted from the tomographic image capturing apparatus 120. Then, the image acquisition unit 210 inputs tomographic image acquired from the tomographic image capturing apparatus 120 to the image processing unit 220 and the storage unit 230 (more specifically, the image storage unit 231).

Subsequently, in step S102, the layer detection unit 221 performs processing for detecting, from the tomographic image acquired in step S101, a boundary of a predetermined layer that constitutes the eye portion (i.e., the object).

An example of a processing method for detecting a boundary of the layer, which can be performed by the layer detection unit 221, is described below. In the present exemplary embodiment, an input three-dimensional tomographic image is regarded as an assembly of two-dimensional tomographic images (i.e., B-scan images) and the layer detection unit 221 executes the following two-dimensional image processing on each of the two-dimensional tomographic image.

First, the layer detection unit 221 performs smoothing filter processing on a target two-dimensional tomographic image to remove noise components. Then, the layer detection unit 221 performs edge detection filter processing to detect edge components from the tomographic image and extract, from each layer, an edge corresponding to a boundary of each layer. For example, the layer detection unit 221 searches an edge from a hyaloid body side in the eyeground depth direction and designates an initial peak position as a boundary between the hyaloid body and a retinal layer. Further, for example, the layer detection unit 221 searches an edge in the eyeground depth direction and designates a final peak position as a boundary of the retinal pigment epithelium. Through the above-described processing, the boundary of the layer can be detected.

As another layer boundary detection method, a dynamic contour method (e.g., Snakes or level set method) can be used to detect the boundary of each layer. For example, the level set method includes defining a level set function having a dimension higher by one than the dimension of an area to be detected and regarding the boundary of a layer to be detected as a zero contour line. The level set method further includes updating the level set function to control the contour and finally detecting the boundary of the layer.

As another layer boundary detection method, a graph theory (e.g., GraphCut) can be used to detect the boundary of each layer. In this case, the method includes setting a node that corresponds to each peak cell of an image and terminals that may be referred to as "sink" and "source." The method further includes setting "edge (n-link)" that connects nodes and "edge (t-link)" that connects terminals. Additionally, the method includes allocating a weighting value to each edge and obtaining a minimum cut from a generated graph and finally detecting the boundary of the layer.

The above-described dynamic contour method or the GraphCut based boundary detection method can be three-dimensionally applied to a three-dimensional tomographic image. Alternatively, when an input three-dimensional tomographic image is regarded as an assembly of two-dimensional tomographic images, the above-described method can be two-dimensionally applied to each two-dimensional tomographic image. Further, in addition to feature quantities of an image, probabilistic atlas or statistical atlas (preliminary knowledge) can be used to detect the boundary of a layer. The layer boundary detection method is not limited to the above-described methods. Any other method is usable if a boundary of a layer can be detected from a tomographic image of an eye portion.

Subsequently, in step S103, the normal structure estimation unit 222 performs processing for estimating a normal structure of the detected layer based on the boundary of a predetermined layer detected in step S102 (i.e., the boundary of the retinal pigment epithelium in the present exemplary embodiment) and features modified by a lesion of the layer.

Figure 5:
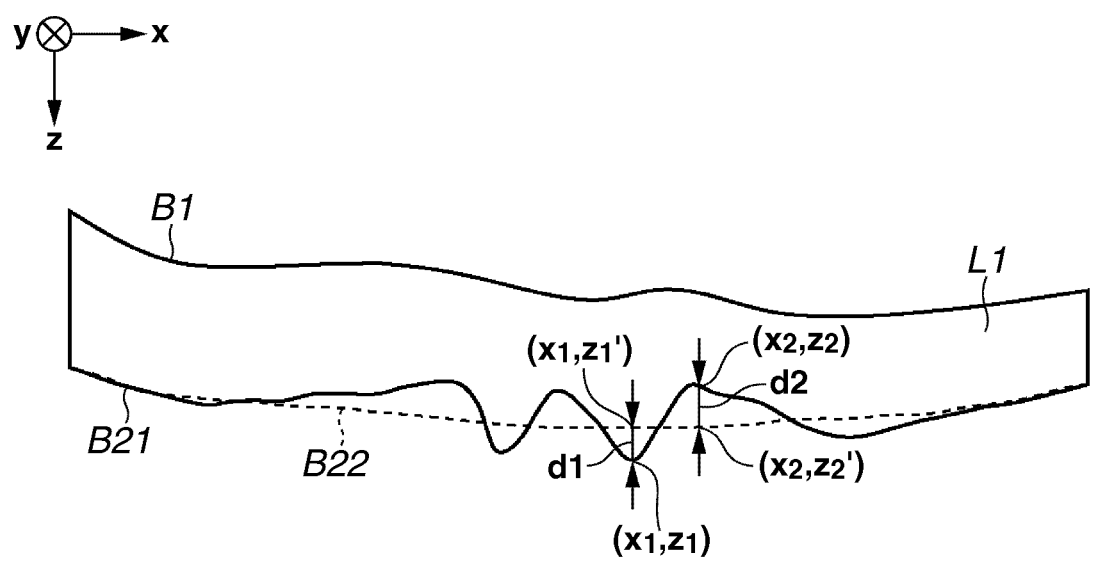
FIG. 5 is a schematic view illustrating estimation of a normal structure of a layer included in a tomographic image according to the first exemplary embodiment of the present invention.

An example processing method for estimating a normal structure of the retinal pigment epithelium to be performed by the normal structure estimation unit 222 is described below with reference to FIG. 5. FIG. 5 is a schematic view illustrating estimation of a normal structure of a layer included in a tomographic image according to the first exemplary embodiment of the present invention.

The tomographic image illustrated in FIG. 5, similar to FIG. 3, includes a layer L1, a layer boundary B1, a layer boundary B21, and an estimated layer boundary B22. Further, in FIG. 5, d1 represents the difference between a coordinate point (x1, z1) of the layer boundary B21 and a coordinate point (x1, z1') of the estimated layer boundary B22 and d2 represents the difference between a coordinate point (x2, z2) of the layer boundary B21 and a coordinate point (x2, z2') of the estimated layer boundary B22. In FIG. 5, at the coordinate position x1, the detected layer boundary B21 is deviated toward a deep portion side of the retinal pigment epithelium compared to the estimated layer boundary B22. At the coordinate position x2, the detected layer boundary B21 is deviated toward a surface side of the retinal pigment epithelium compared to the estimated layer boundary B22.

The normal structure estimation by the normal structure estimation unit 222 is performed without causing the layer boundary B21 (i.e., the detection result obtained by the layer detection unit 221) to protrude below the normal structure B22, except for a detection error value. This is, first, because a deformation of the retinal pigment epithelium to be caused by age-related macular degeneration is caused by a neogenetic blood vessel generated below the retinal pigment epithelium. Second, because the position of the deformed layer boundary is positioned on an upper side compared to the normal position.

An example of the normal structure estimation method according to the present exemplary embodiment includes assuming that an input three-dimensional tomographic image is an assembly of two-dimensional tomographic images (i.e., B-scan images) and estimating a normal structure of each two-dimensional tomographic image, as described below. Further, the method according to the present exemplary embodiment includes estimating a normal structure by applying a secondary function to a group of coordinate points that represent a layer boundary detected in a target two-dimensional tomographic image. In this case, the normal structure can be approximated using a function that represents a quadratic curve in each two-dimensional tomographic image.

The features of the above-described method is not only giving weighting values to differences (distances) between respective points in the group and the function, in applying the function to the group of detected coordinate points, but also changing the weighting value to be used according to the sign of the difference. For example, the normal structure estimation unit 222 selects a weighting function to be used, using the following formula (1).

$$\varepsilon_i = z_i - z_i' \quad (1)$$
$$= z_i - (ax_i^2 + bx_i + c)$$
$$\text{if } \varepsilon_i > 0 \quad \rho_1$$
$$\text{else} \quad \rho_2$$

In the formula (1), zi represents a z-coordinate value of a layer boundary detected at a coordinate point xi, zi' represents a z-coordinate value of its normal structure estimated at the coordinate point xi, and ϵi represents the difference between zi and zi'. Further, the formula (1) includes parameters a, b, and c for the estimating function. Weighting functions ρ1 and ρ2 are positive definite even functions that have only one minimum value at the point x=0. The weighting function can be selected according to the sign of ϵi as indicated by the formula (1).

In FIG. 5, the distances d1 and d2 are different in sign although they are similar in magnitude (ϵ1 is positive and ϵ2 is negative). Therefore, weighting functions to be used are different from each other. According to the example illustrated in FIG. 5, the weighting function ρ1 is used for the distance d1 and the weighting function ρ2 is used for the distance d2. Further, it is desired to estimate a normal structure so as to satisfy a relationship ϵi≤0. Therefore, setting of the weighting function is performed in such a manner that the weighting value becomes larger at a deep portion z of the retina that is deeper than a portion z'. In other words, it is desired to define the weighting functions ρ1 and ρ2 so as to satisfy a relationship ρ1 (ϵi)≥ρ2 (−ϵi) at the difference ϵi. Further, regarding the selection of a weighting function, any function can be used if it satisfies the above-described conditions (i.e., the conditions resulting from the features modified by a lesion of a layer that constitutes an eye portion (i.e., the retinal pigment epithelium in the present exemplary embodiment).

The following formula (2) is an example of an evaluation formula that can be used to obtain an appropriate function.

$$M = \min \sum_i \rho(\varepsilon_i) \quad (2)$$

Figure 6A:
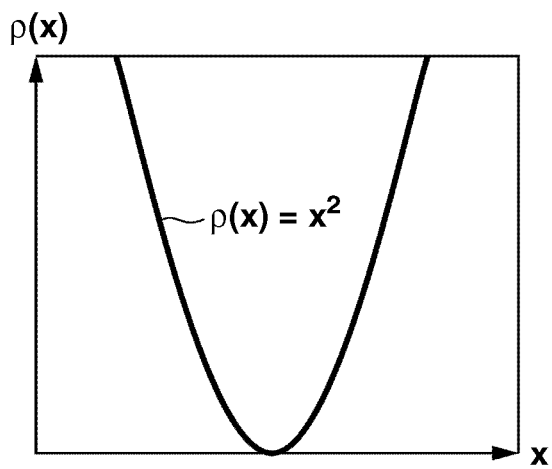
FIGS. 6A, 6B, and 6C are schematic views illustrating weighting functions that can be used to estimate a normal structure of a layer included in a tomographic image according to the first exemplary embodiment of the present invention.
Figure 6B:
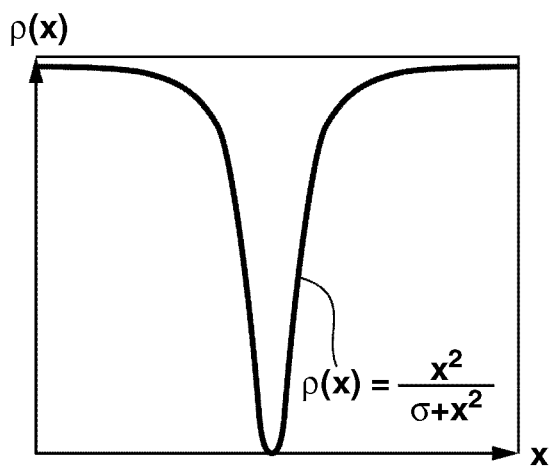
Figure 6C:
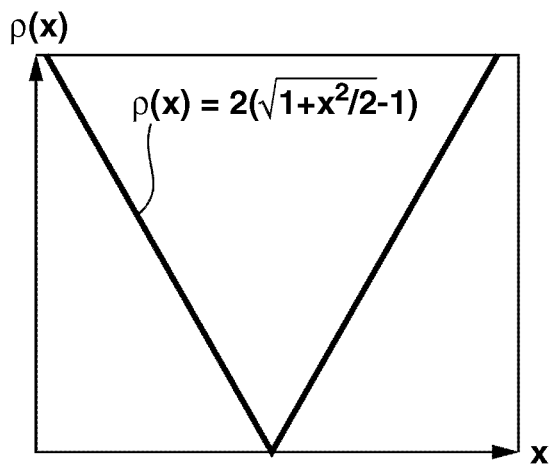

In the formula (2), ρ(ϵi) is a weighting function (i.e., ρ1 or ρ2) selected according to the sign of ϵi. FIGS. 6A, 6B, and 6C illustrate examples of the weighting function that can be used to estimate a normal structure of a layer included in a tomographic image according to the first exemplary embodiment of the present invention.

In FIGS. 6A, 6B, and 6C, the abscissa axis (i.e., x-axis) represents the difference ϵi and the ordinate axis represents the weighting function ρ(x). The weighting function to be used in estimating a normal structure of a layer included in a tomographic image is not limited to the examples illustrated in FIGS. 6A, 6B, and 6C. Any other function can be set. Further, it is useful to differentiate the weighting function ρ(x) to confirm a weighting value to be actually given by the weighting function ρ(x). In the present exemplary embodiment, the normal structure estimation unit 222 estimates the function so as to minimize an evaluation value M defined by the above-described formula (2).

Selecting an appropriate weighting function according to the sign of the difference as described above is useful to prevent the layer boundary B21 detected by the layer detection unit 221 from protruding below the normal structure B22 estimated by the normal structure estimation unit 222, as illustrated in FIG. 3. Then, as a result, the normal structure estimation unit 222 can accurately perform estimation of a normal structure.

The above-described estimation method according to the present exemplary embodiment regards an input three-dimensional tomographic image as an assembly of two-dimensional tomographic images (i.e., B-scan images) and estimates a normal structure based on each two-dimensional tomographic image. However, the normal structure estimation method is not limited to the above-described method. For example, the normal structure estimation method may include processing to be performed on a three-dimensional tomographic image. In this case, the method includes applying an elliptic body to the group of three-dimensional coordinate points that represent the boundary of a layer detected in step S102, while using a similar weighting function selection standard. The shape that approximates a normal structure is not limited to a secondary function and can be estimated using any other function.

Subsequently, referring back to the description of FIG. 4, in step S104, the quantification unit 223 performs various types of quantification processing. First, the quantification unit 223 performs processing for calculating the layer thickness T1 of the layer L1 illustrated in FIG. 3, in addition to the area and the volume of the layer L1, based on the layer boundary detected by the layer detection unit 221 in step S102. In this case, the quantification unit 223 can calculate the layer thickness T1 by obtaining an absolute value that represents a z-coordinate difference between the layer boundary B1 and the layer boundary B21 at each coordinate point on the x-y plane. Further, the quantification unit 223 can calculate the area of the layer L1 by successively adding layer thicknesses at each coordinate point in the x-axis direction for each y-coordinate. Further, the quantification unit 223 can calculate the volume of the layer L1 by successively adding obtained areas along the y-axis direction.

Further, the quantification unit 223 quantifies the turbulence of the retinal pigment epithelium detected in step S102 based on the boundary B21 of the retinal pigment epithelium detected by the layer detection unit 221 in step S102 and the normal structure B22 estimated by the normal structure estimation unit 222 in step S103.

More specifically, the quantification unit 223 calculates a difference T2 (see FIG. 3) between the structure of B21 and the structure of B22 at each coordinate point on the x-y plane, as a z-coordinate difference between two structures. Then, the quantification unit 223 successively adds the obtained difference T2 along the x-axis direction for each y-coordinate to obtain an area derived from the difference. Further, the quantification unit 223 successively adds the obtained area along the y-axis direction to calculate a volume derived from the difference. In the present exemplary embodiment, the feature quantity that represents the turbulence of the retinal pigment epithelium can be any other feature quantity that can quantify the difference between the structure of B21 and the structure of B22.

For example, a maximum value, a central value, a variance, an average, or a standard deviation of the obtained difference T2, or any other value (e.g., the number (or ratio) of points that are equal to or greater than a threshold) can be obtained and used as the feature quantity that represents the turbulence of the retinal pigment epithelium. Further, an average density value, a density variance value, or a contrast value can be obtained as a feature representing the density of an area defined by B21 and B22.

Figure 7:
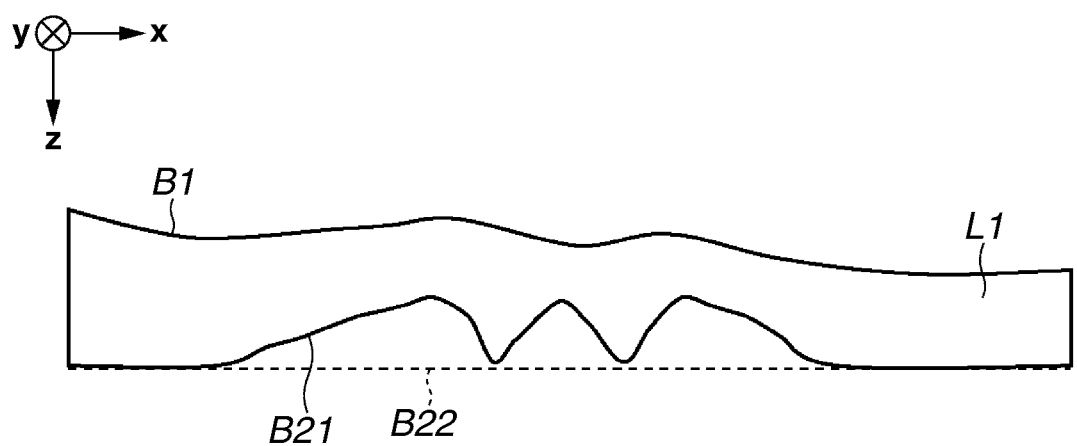
FIG. 7 is a schematic view illustrating an example of processing for converting a tomographic image into a flat plane according to the first exemplary embodiment of the present invention.

Further, another quantification method to be realized by the quantification unit 223 includes converting the boundary of a layer into a flat plane that can be used as a reference position in the quantification processing, as illustrated in FIG. 7. FIG. 7 is a schematic view illustrating processing for converting a tomographic image into a flat plane according to the first exemplary embodiment of the present invention. More specifically, the layer boundary conversion illustrated in FIG. 7 is a conversion of the deepest boundary B22 of the retinal layer illustrated in FIG. 3 (e.g., the boundary of the retinal pigment epithelium) into a flat plane. In this case, conversion of other layer is performed according to its deformation.

Further, the quantification unit 223 performs comparison between past and present quantification data, for example, with respect to layer thickness, layer area, layer volume, shape features, and density features, if such quantification data have been obtained in the past. An example method for comparing past and present quantification data is described below.

In this case, first, the quantification unit 223 performs alignment between past and present tomographic images. In this case, a conventionally known method, such as rigid affine transformation or a nonlinear type Free Form Deformation (FFD), can be used for the alignment of tomographic images. If the positional relationship between the past tomographic image and the present tomographic image is in good shape, the quantification unit 223 can perform comparisons with respect to the layer thickness and the layer area at an arbitrary cross section as well as the volume of an arbitrary area.

In the present exemplary embodiment, the quantification unit 223 compares various data after finishing the alignment between past and present tomographic images. However, the quantification unit 223 can omit the above-described alignment, for example, if the tomographic image capturing apparatus 120 has a tracking function to capture an image of a position that was captured in the previous imaging operation. Further, instead of performing the above-described alignment, the quantification unit 223 can simply compare slice numbers of B-scan images or can perform comparison with respect to 3D.

In the present exemplary embodiment, the quantification unit 223 obtains at least one of the above-described numerical data. The data to be quantified can be arbitrarily set. If the quantification unit 223 cannot obtain any one of the above-described numerical data, then in the next step S105, the quantification unit 223 can cause the display unit 240 to display a message that notifies failure in the quantification.

Subsequently, referring back to the description of FIG. 4, in step S105, the display unit 240 performs processing for displaying the tomographic image, a detection result with respect to the boundary between two layers captured in the tomographic image, an estimation result with respect to the normal structure, and a quantification result with respect to the layer captured in the tomographic image. The display unit 240 according to the present exemplary embodiment can be configured to include the monitor 115. Therefore, in the processing of step S105, various data can be displayed on the monitor 115. In the present exemplary embodiment, if there are any data obtained in the past, the display to be realized by the monitor 115 can be arranged to realize a comparison between the past and present data.

Figure 8:
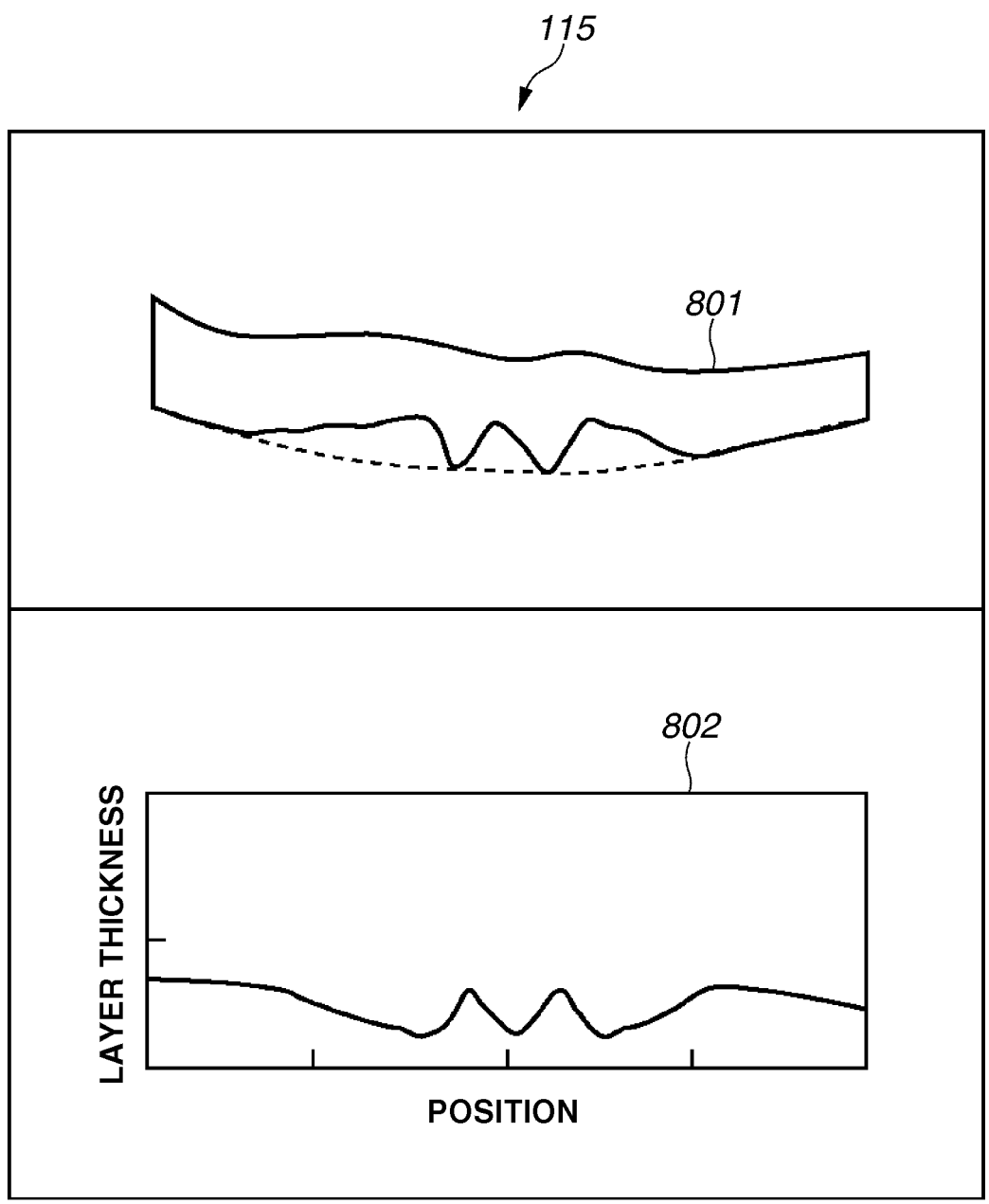
FIG. 8 is a schematic view illustrating an example of displayed image processing results according to the first exemplary embodiment of the present invention, which can be obtained by the image processing apparatus illustrated in FIG. 1.

FIG. 8 is a schematic view illustrating an example of displayed image processing results according to the first exemplary embodiment of the present invention, which can be obtained by the image processing apparatus 110-1 illustrated in FIG. 1. The example display illustrated in FIG. 8 includes a tomographic image 801 to be displayed on an upper side of the monitor 115, which represents a layer-to-layer boundary detected by the image processing unit 220 and an estimated normal structure, and a graph 802 to be displayed on a lower side of the monitor 115, which indicates the thickness of a retinal layer as an analysis result on the tomographic image 801.

As another example display for a tomographic image, the layer-to-layer boundary detected by the image processing unit 220 and the estimated normal structure can be superimposed on the tomographic image acquired by the image acquisition unit 210. Further, as another example display for a tomographic image, it is useful to convert the boundary of a specific layer into a flat plane serving as a reference plane and then generate a tomographic image to be displayed based on the reference plane (see FIG. 7). The range of a layer to be modified is comparable to a piece of B-scan image or a three-dimensional tomographic image.

Subsequently, referring back to the description of FIG. 4, in step S106, the storage unit 230 (e.g., the data storage unit 232) associate various data acquired in the above-described steps S101 to S104 and stores the associated data as patient data of a patient in the magnetic disk 113. More specifically, the tomographic image data obtained in step S101, the layer-to-layer boundary data obtained in step S102, the layer normal structure data estimated in step S103, and the layer quantification processing result obtained in step S104 are associated with each other as data to be stored. In the present exemplary embodiment, the data stored in the magnetic disk 113 is at least one of the above-described data.

In this case, it is useful to store a normal structure estimation result together with the data used in the estimation, such as the weighting function p (see formula (1)) and the function parameters (e.g., a, b, and c in the formula (1)) that are associated with each other. The stored data (i.e., the function and the parameters) can be reused in estimation for progress observation to be performed.

Further, the above-described data can be stored in an external server (not illustrated). In this case, the storage unit 230 transmits these data to the external server.

In the present exemplary embodiment, the layers to be detected by the layer detection unit 221 are not limited to the inner limiting membrane and the retinal pigment epithelium. The layer detection unit 221 can detect other layers (e.g., a nerve fiber layer and a photoreceptor layer) and other membrane (e.g., an outer limiting membrane). Further, the layer boundary to be used to estimate a normal structure is not limited to the retinal pigment epithelium. Any other layer having a contour that changes into a wavy shape due to a disease can be used in the estimation.

As apparent from the foregoing description, the above-described first exemplary embodiment can accurately estimate the normal structure of a layer that constitutes the eye portion (e.g., the retinal pigment epithelium in the present exemplary embodiment) from a tomographic image of the eye portion (i.e., the object). Thus, the first exemplary embodiment can accurately quantify the stage of a disease in the eye portion or the degree of recovery from the disease after treatment.

The image processing apparatus 110-1 according to the first exemplary embodiment can be configured, as its first modified example, to include an image storage server (not illustrated) that stores tomographic images of eye portions that are stored in an already captured state and input, directly or via the LAN 130, a tomographic image from the image storage server. In this case, in step S101 of FIG. 4, the image acquisition unit 210 requests the image storage server to transmit a designated tomographic image and acquires the tomographic image transmitted from the image storage server, and then inputs the acquired image to the storage unit 230. Subsequently, the layer boundary detection (see step S102) and the quantification processing (see S104) are performed, as described above.

The image processing apparatus 110-1 according to the first exemplary embodiment can be configured, as its second modified example, to input one or a plurality of two-dimensional tomographic images and perform the above-described analysis processing (i.e., image processing) on each input image. Further, it is useful to select a target cross section from an input three-dimensional tomographic image and perform the processing on the selected two-dimensional tomographic image. In this case, a user can select a desired two-dimensional tomographic image by operating the mouse 116 or the keyboard 117, or using an interface (not illustrated). Further, the processing can be applied to a predetermined specific portion of the eyeground (e.g., across section that includes the center of a macula lutea portion).

Figure 9:
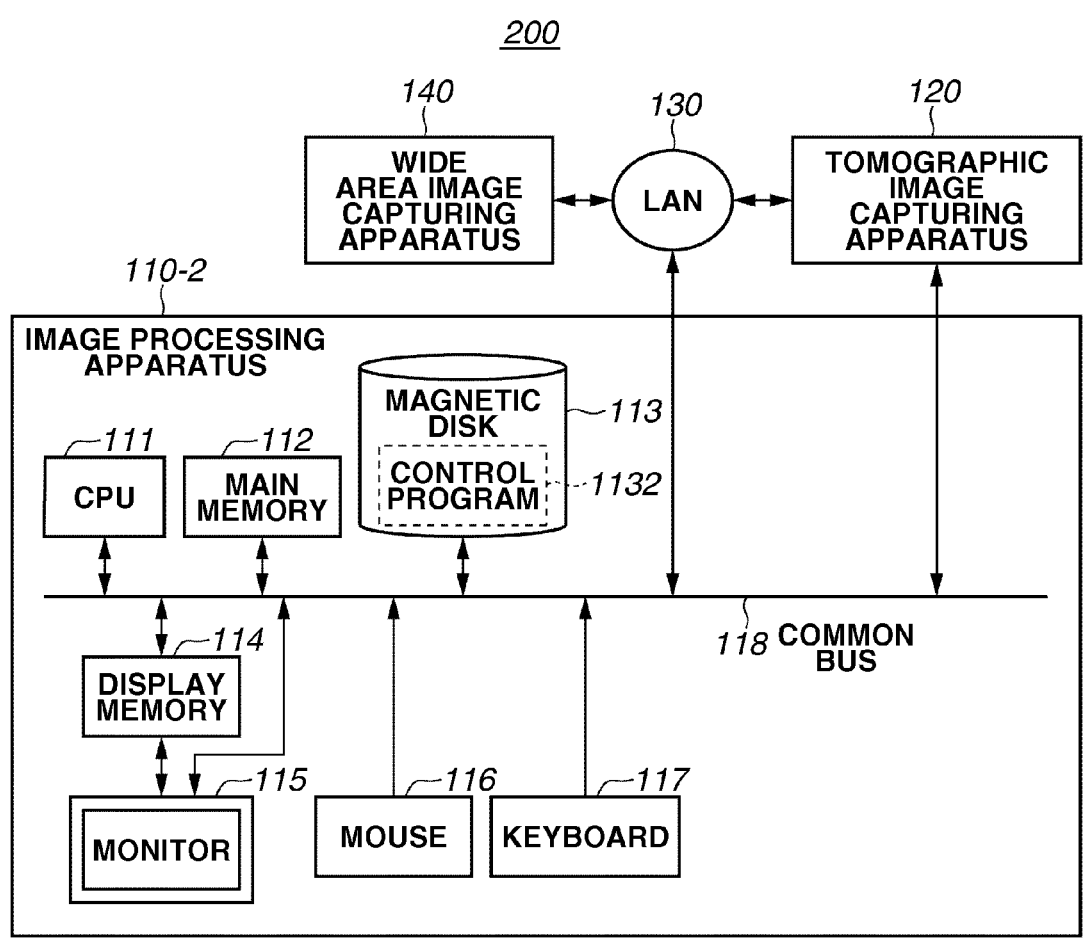
FIG. 9 is a schematic view illustrating an example of a schematic configuration (a hardware configuration) of an image processing system according to a second exemplary embodiment of the present invention.

Next, a second exemplary embodiment of the present invention is described below in detail. FIG. 9 is a schematic view illustrating an example of a schematic configuration (a hardware configuration) of an image processing system 200 according to the second exemplary embodiment of the present invention.

As illustrated in FIG. 9, the image processing system 200 according to the present exemplary embodiment includes an image processing apparatus 110, a tomographic image capturing apparatus 120, a local area network (LAN) 130, and a wide area image capturing apparatus 140. In the following description, the image processing apparatus 110 illustrated in FIG. 9 is referred to as an "image processing apparatus 110-2." More specifically, according to the image processing system 200 illustrated in FIG. 9, the image processing apparatus 110-2 is connected not only to the tomographic image capturing apparatus 120 but also to the wide area image capturing apparatus 140 via the LAN 130. The connection between the image processing apparatus 110-2 and the wide area image capturing apparatus 140 can be realized, for example, by using an appropriate interface (e.g., USB and IEEE1394)

Similar to the above-described image processing apparatus 110-1 according to the first exemplary embodiment, the image processing apparatus 110-2 according to the present exemplary embodiment detects a layer boundary (e.g., a boundary of the retinal pigment epithelium) from a tomographic image of an eye portion. Further, similar to the image processing apparatus 110-1 according to the first exemplary embodiment, the image processing apparatus 110-2 estimates a normal structure of the retinal pigment epithelium, for example, based on features such that the shape of the layer changes into a wavy shape due to a disease (e.g., age-related macular degeneration). Then, the image processing apparatus 110-2 quantifies the disease based on an estimation result.

The image processing apparatus 110-2 according to the present exemplary embodiment determines whether the shape of the retinal pigment epithelium detected from the tomographic image of the eye portion is normal or abnormal for each local area. The image processing apparatus 110-2 estimates the normal structure of the retinal pigment epithelium based on information obtained from a normal range (i.e., a range having been determined as being normal). To this end, the image processing apparatus 110-2 illustrated in FIG. 9 stores a control program 1132, which is different from the control program 1131 described in the first exemplary embodiment, in the magnetic disk 113.

The wide area image capturing apparatus 140 is, for example, an apparatus that captures a wide area image including an eye portion. For example, the wide area image capturing apparatus 140 includes an eyeground camera. A wide area image capturing apparatus 140 captures a wide area image including an eye portion of a subject (i.e., a patient (not illustrated)) according to an operation of a user (e.g., an engineer or a physician). Then, the wide area image capturing apparatus 140 outputs the obtained wide area image to the image processing apparatus 110-2.

Figure 10:
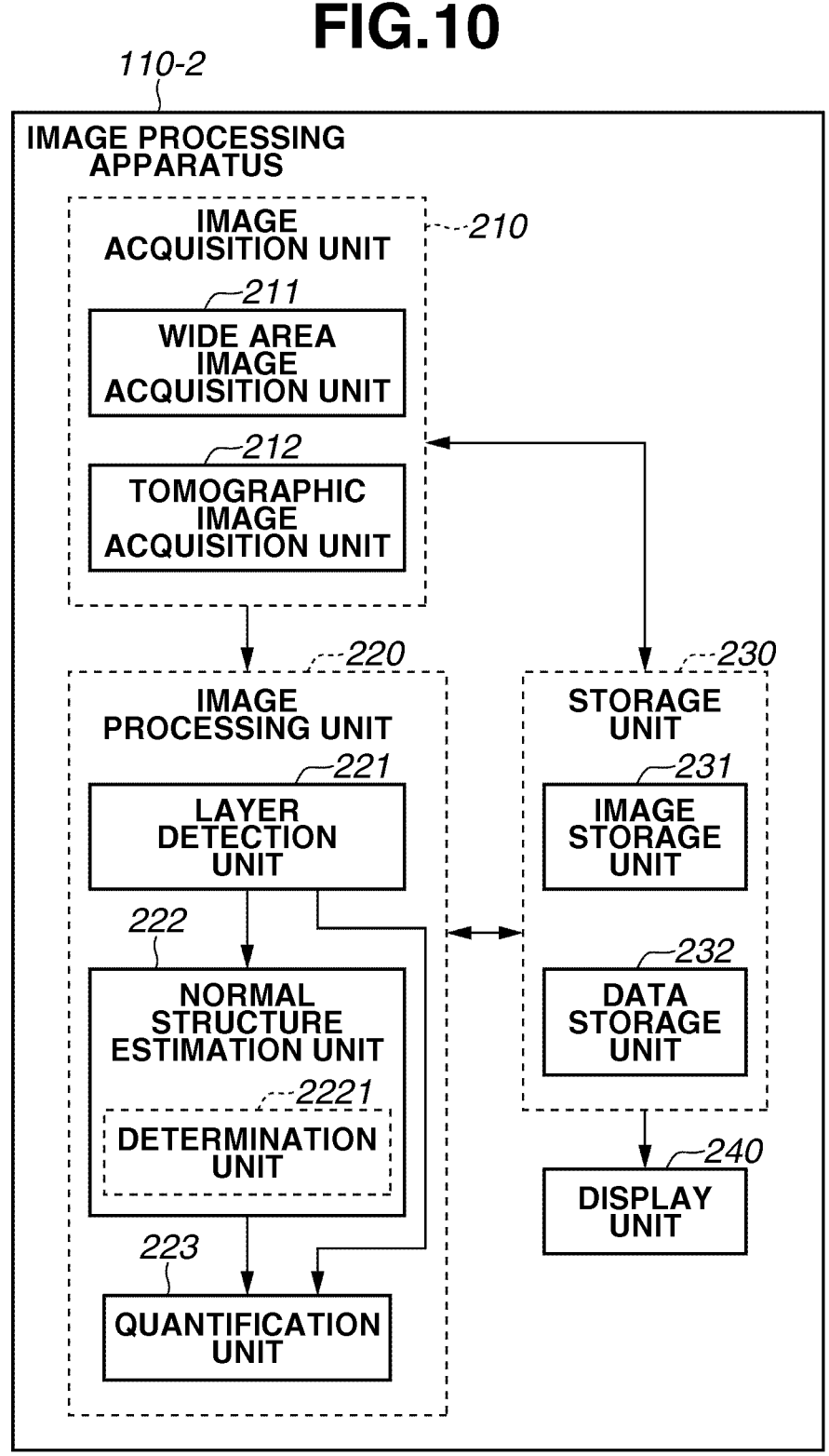
FIG. 10 is a schematic view illustrating an example of a functional configuration of the image processing apparatus according to the second exemplary embodiment of the present invention.

Next, a functional configuration of the image processing apparatus 110-2 illustrated in FIG. 9 is described below. FIG. 10 is a schematic view illustrating an example of the functional configuration of the image processing apparatus 110-2 according to the second exemplary embodiment of the present invention.

As illustrated in FIG. 10, the image processing apparatus 110-2 includes an image acquisition unit 210, an image processing unit 220, a storage unit 230, and a display unit 240, as constituent components that constitute the functional configuration. The functional configuration of the image processing apparatus 110-2 according to the second exemplary embodiment is basically similar to the functional configuration of the image processing apparatus 110-1 according to the first exemplary embodiment (see FIG. 2). However, in the image processing apparatus 110-2 according to the second exemplary embodiment, the image acquisition unit 210 includes a wide area image acquisition unit 211 and a tomographic image acquisition unit 212. Further, a normal structure estimation unit 222 provided in the image processing unit 220 includes a determination unit 2221 that can determine whether the shape of a layer is normal or abnormal.

Figure 11:
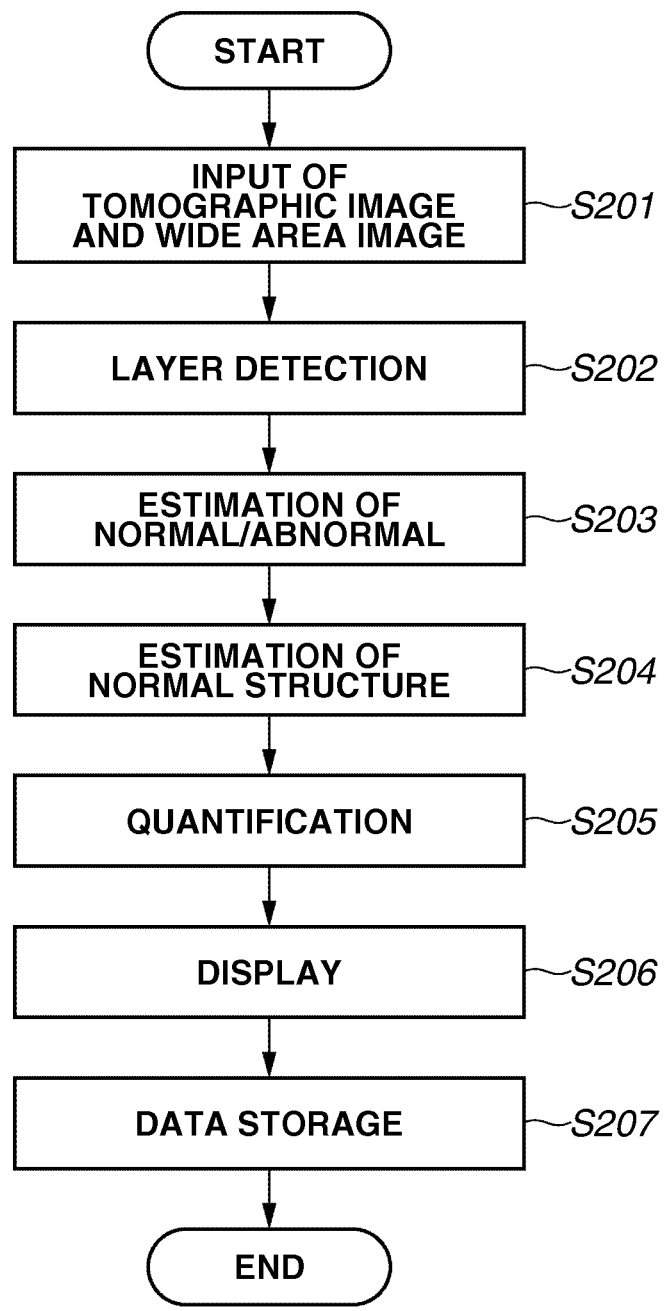
FIG. 11 is a flowchart illustrating an example of a processing procedure of a method for controlling an image processing apparatus according to the second exemplary embodiment of the present invention.

Next, an example procedure of processing to be executed by the image processing apparatus 110-2 according to the present exemplary embodiment is described below with reference to FIG. 11. FIG. 11 is a flowchart illustrating an example of a processing procedure of a method for controlling the image processing apparatus 110-2 according to the second exemplary embodiment of the present invention.

First, in step S201, the tomographic image acquisition unit 212 requests the tomographic image capturing apparatus 120 to transmit a tomographic image of an eye portion (i.e., an object) and acquires the tomographic image of the eye portion transmitted from the tomographic image capturing apparatus 120. Then, the tomographic image acquisition unit 212 inputs the tomographic image acquired from the tomographic image capturing apparatus 120 to the image processing unit 220 and the storage unit 230 (more specifically, the image storage unit 231). Similarly, the wide area image acquisition unit 211 requests the wide area image capturing apparatus 140 to transmit a wide area image of the eye portion (i.e., the object) and acquires the wide area image of the eye portion transmitted from the wide area image capturing apparatus 140. Then, the wide area image acquisition unit 211 inputs the acquired wide area image to the image processing unit 220 and the storage unit 230 (more specifically the image storage unit 231).

Subsequently, in step S202, the layer detection unit 221 performs processing for detecting, from the tomographic image acquired in step S201, a boundary of a predetermined layer that constitutes the eye portion (i.e., the object). In the present exemplary embodiment, the layer detection method is similar to that described in the first exemplary embodiment as can be understood by referring to the processing to be performed in step S102 illustrated in FIG. 4. In this case, it is useful to extract a lesion or a blood vessel from the wide area image and detect a layer boundary based on information obtained from the extracted lesion or blood vessel, without solely relying on the tomographic image.

Subsequently, in step S203, the determination unit 2221 in the normal structure estimation unit 222 detects (determines) whether the layer boundary detected by the layer detection unit 221 in step S202 (i.e., the boundary (B21) of the retinal pigment epithelium in the present exemplary embodiment) is a normal range and an abnormal range. Then, the determination unit 2221 classifies the layer boundary detected by the layer detection unit 221 in step S202 between the normal range and the abnormal range.

More specifically, for example, as a first condition that can be referred to in identifying a layer as having a normal structure, it can be defined that the layer boundary has a smooth curvature. In this case, to detect an abnormal range, the determination unit 2221 calculates a local curvature of a detected layer boundary and evaluates the shape of the layer boundary. If there is any portion where the curvature does not smoothly change, the determination unit 2221 identifies this portion as an abnormal range. Alternatively, to detect an abnormal range, the determination unit 2221 can detect a facula, a bleeding, or a drusen from the wide area image of the eye portion and determine a retinal layer structure extending along the z-direction of the tomographic image, which corresponds to an area (x, y) of the wide area image where the presence of a lesion is recognized, as being abnormal. Then, the determination unit 2221 classifies the position of the normal range and the position of the abnormal range in the tomographic image.

Subsequently, in step S204, the normal structure estimation unit 222 performs processing for estimating a normal structure of the layer based on the layer boundary included in the normal range determined in step S203 and the features modified by a lesion of the layer.

Similar to the processing of step S103 in FIG. 4 in the first exemplary embodiment, the normal structure estimation method in step S204 includes performing estimation using a polynomial expression to approximate a normal structure. In this case, the normal structure estimation unit 222 calculates parameters of the polynomial expression based on only the group of coordinate points that have been determined as being normal by the determination unit 2221, to approximate the normal structure. Alternatively, instead of using the polynomial expression, the normal structure estimation unit 222 can estimate a normal structure by performing interpolation processing (e.g., spline interpolation) on the group of coordinate points that have been determined as being normal by the determination unit 2221.

Subsequently, in step S205, the quantification unit 223 performs various types of quantification processing, which is similar to the processing of step S104 illustrated in FIG. 4 that has been described in the first exemplary embodiment.

Subsequently, in step S206, the display unit 240 performs display processing that is basically similar to the processing of step S105 illustrated in FIG. 4 that has been described in the first exemplary embodiment. In this case, in the present exemplary embodiment, arbitrary information can be selected for the display of the estimated normal structure and the detected layer boundary. Example displays are described below with reference to FIGS. 12A to 12D.

FIGS. 12A to 12D are schematic views illustrating examples of the boundary of a layer included in a tomographic image according to the second exemplary embodiment of the present invention. In each of FIGS. 12A to 12D, a solid line indicates a layer boundary detected by the layer detection unit 221 and a dotted line indicates a normal structure estimated by the normal structure estimation unit 222.

Figure 12A:
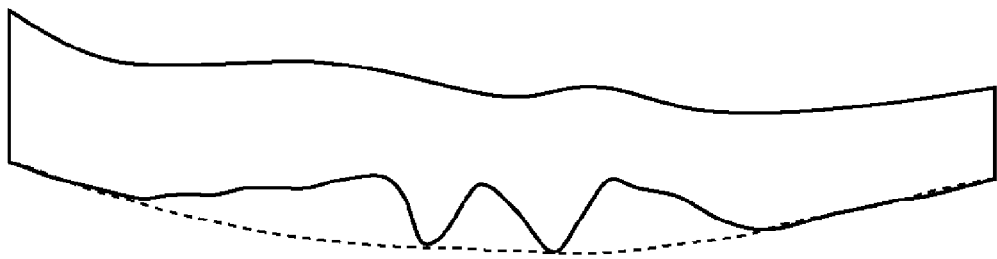
FIGS. 12A, 12B, 12C, and 12D are schematic views illustrating examples of the boundary of a layer included in a tomographic image according to the second exemplary embodiment of the present invention.
Figure 12B:
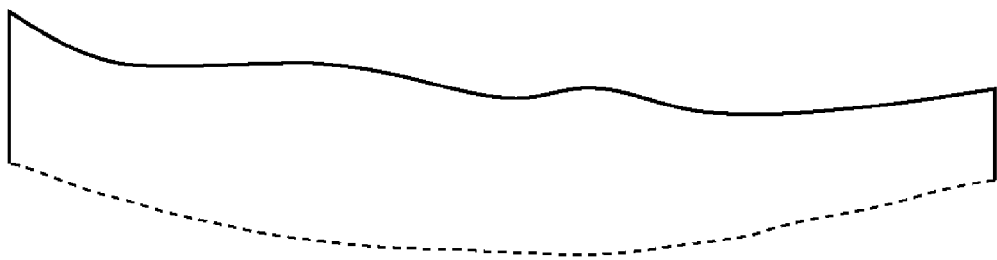
Figure 12C:
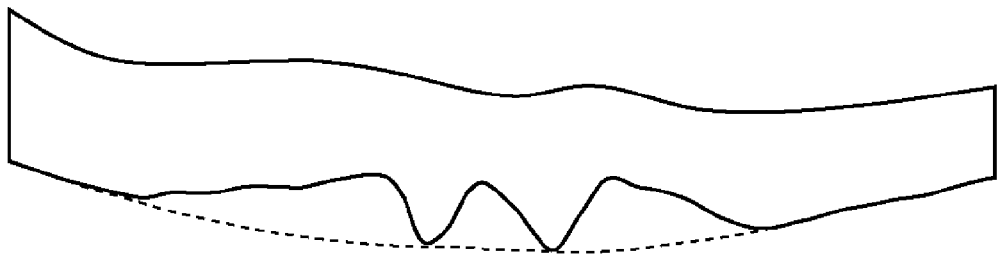
Figure 12D:
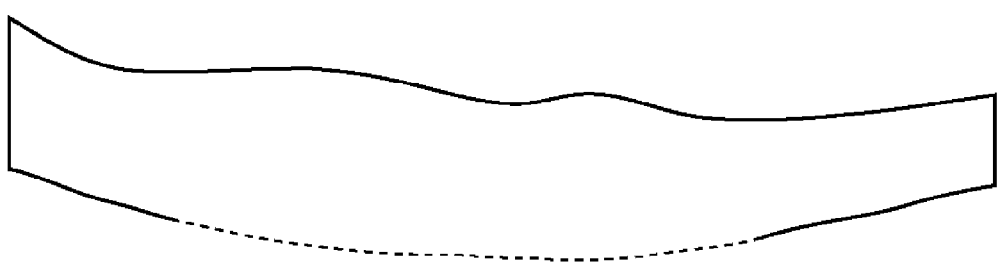

More specifically, according to an example illustrated in FIG. 12A, both a detected layer boundary and an estimated normal structure are simultaneously displayed. According to an example illustrated in FIG. 12B, only an estimated normal structure is displayed. According to an example illustrated in FIG. 12C, with respect to the same layer boundary, a detected layer boundary is displayed in the normal range while both a detected layer boundary and an estimated normal structure are simultaneously displayed in the abnormal range. According to an example illustrated in FIG. 12D, with respect to the same layer boundary, a detected layer boundary is displayed in the normal range while only an estimated normal structure is displayed in the abnormal range.

As an example of the display method employable in step S206, the detection results and the estimation results illustrated in FIGS. 12A to 12D can be superimposed on a tomographic image. As another example of the display method employable in step S206, the detection results and the estimation results can be displayed separately from the tomographic image. In this manner, arbitrary information can be displayed by appropriately selecting a display method for the information relating to the layer boundary.

Subsequently, in step S207, the storage unit 230 performs storage processing that is basically similar to the processing of step S106 illustrated in FIG. 4 that has been described in the first exemplary embodiment. In this case, for the purpose of letting users confirm an image capturing portion, it is useful to store and display the wide area image in association with a tomographic image acquisition range in the wide area image.

As apparent from the foregoing description, the second exemplary embodiment determines whether the structure of the retinal pigment epithelium is normal or abnormal for each local area in the tomographic image of the eye portion (i.e., the object). Therefore, the second exemplary embodiment can accurately estimate the normal structure of a layer, even if the layer has changed due to a disease, based on information of the area having been determined as being normal. Thus, the second exemplary embodiment can accurately quantify the stage of a disease or the degree of recovery from the disease after treatment based on the result of estimation.

Next, a third exemplary embodiment of the present invention is described below in detail. A schematic configuration of an image processing system according to the third exemplary embodiment is similar to that of the image processing system 100 (see FIG. 1) according to the first exemplary embodiment. Further, a functional configuration of the image processing apparatus 110 according to the third exemplary embodiment is basically similar to the functional configuration of the image processing apparatus 110-1 (see FIG. 2) according to the first exemplary embodiment. However, processing to be performed by the normal structure estimation unit 222 is different from that of the above-described embodiment. In the present exemplary embodiment, the image processing apparatus 110 according to the third exemplary embodiment is referred to as an "image processing apparatus 110-3."

Further, similar to the above-described image processing apparatus 110-1 according to the first exemplary embodiment, the image processing apparatus 110-3 according to the present exemplary embodiment detects a layer boundary (e.g., a boundary of the retinal pigment epithelium) from a tomographic image of an eye portion. Further, similar to the image processing apparatus 110-1 according to the first exemplary embodiment, the image processing apparatus 110-3 estimates a normal structure of the retinal pigment epithelium, for example, based on features such that the shape of the layer changes into a wavy shape due to a disease (e.g., age-related macular degeneration). Thus, the image processing apparatus 110-3 quantifies the disease based on an estimated result.

However, in the estimation of the normal structure, the image processing apparatus 110-3 according to the present exemplary embodiment presumes the shape of the boundary of the retinal pigment epithelium detected from the tomographic image of the eye portion as a mixed distribution composed of a single polynomial function that represents the normal structure and a total of n Gaussian functions each having a shape protruding upward to represent a lesion. More specifically, the wavy shape of a layer caused by the growth of each protrusion can be adequately approximated using Gaussian functions while the rest of the layer shape can be roughly estimated using a single polynomial expression.

The normal structure estimation unit 222 (see FIG. 2) according to the present exemplary embodiment presumes that the shape of a layer boundary is a mixed distribution composed of a secondary function that represents a normal structure and n Gaussian functions in approximating a detected group of coordinate points. Then, the normal structure estimation unit 222 according to the present exemplary embodiment estimates the mixed distribution to identify a normal structure of a layer whose shape has changed into a wavy shape. An example is illustrated in FIGS. 13A and 13B.

Figure 13A:
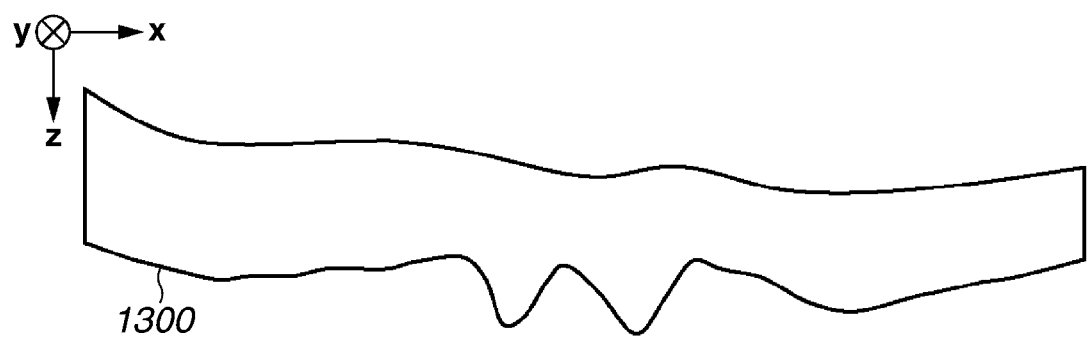
FIGS. 13A and 13B are schematic views illustrating estimation of a normal structure of a layer included in a tomographic image according to a third exemplary embodiment of the present invention.
Figure 13B:

FIGS. 13A and 13B are schematic views illustrating example estimation of a normal structure of a layer included in a tomographic image according to the third exemplary embodiment of the present invention. More specifically, FIG. 13A illustrates an example boundary shape 1300 of the retinal pigment epithelium that has changed due to age-related macular degeneration. FIG. 13B illustrates a polynomial expression 1301 and Gaussian functions 1302, which can be obtained from the boundary shape 1300 of the retinal pigment epithelium illustrated in FIG. 13A.

For example, the EM algorithm can be used to solve the mixed distribution composed of the secondary function and the Gaussian functions. In this case, the mixed distribution is regarded as a probability model that combines a polynomial expression and a plurality of Gaussian functions, in which weighting values are given to probabilities of the polynomial expression and the Gaussian functions.

The normal structure estimation unit 222 according to the present exemplary embodiment uses the EM algorithm to estimate parameters (e.g., a, b, and c) of the secondary function, parameters (e.g., average and variance-covariance matrix) of Gaussian functions, a mixing rate of the secondary function and Gaussian functions. In this case, setting of n Gaussian functions can be performed to set n according to the number of negative peaks with respect to the sign of the difference between the polynomial expression and a detected layer boundary. Alternatively, it is also useful to set the number n that can maximize the evaluation value while the number n is increased from 1 to N.

Further, according to the EM algorithm, a provisional parameter is set as an initial value, then the validity of the provisional parameter is determined in Estep, and a parameter improving the validity is selected in Mstep. In the present exemplary embodiment, the parameter is finally selected at the time when the calculation has converged by repeating the above-described Estep and Mstep. In the present exemplary embodiment, the validity is determined based on the likelihood at the moment. The parameter selection is performed by selecting a parameter that is larger than the likelihood at the moment.

In the present exemplary embodiment, n Gaussian functions each having a shape protruding upward are mixed with a single smooth secondary function. More specifically, the present exemplary embodiment approximates a wavy shape of a layer caused by the growth of each protrusion using Gaussian functions and roughly approximates the rest of the layer shape using a single polynomial expression. According to the above-described method, an input three-dimensional tomographic image is regarded as an assembly of two-dimensional tomographic images (i.e., B-scan images) and a normal structure is estimated for each two-dimensional tomographic image.

However, the normal structure estimation method is not limited to the above-described method. For example, an input three-dimensional tomographic image can be directly processed. Further, the function to be used in approximating a normal structure is not limited to a secondary function. The shape of a layer can be estimated using any other function. Further, the boundary of a layer to be used to estimate a normal structure is not limited to that of the retinal pigment epithelium. Any other layer (or layer boundary) can be used if its shape changes into a wavy shape due to a disease.

Each constituent component illustrated in FIG. 2 and FIG. 10, which constitutes the image processing apparatus 110 in the above-described exemplary embodiments of the present invention, and each step in FIG. 4 and FIG. 11 can be realized by the CPU 111, when the CPU 111 executes the control program stored in the magnetic disk 113. In this respect, the present invention encompasses the control program and a computer-readable storage medium that stores the control program (e.g., the magnetic disk 113 in the exemplary embodiment).

Next, a fourth exemplary embodiment of the present invention is described below in detail.

FIG. 14 is a schematic view illustrating an example of a functional configuration of the image processing apparatus 110 according to the fourth exemplary embodiment of the present invention, which is referred to as an "image processing apparatus 110-4."

As illustrated in FIG. 14, the image processing apparatus 110-4 includes an object information acquisition unit 2100, an image acquisition unit 2200, an instruction acquisition unit 2300, a storage unit 2400, an image processing unit 2500, a display unit 2600, and a result output unit 2700, as constituent components that constitute the functional configuration.

In the present exemplary embodiment, for example, the object information acquisition unit 2100 and the instruction acquisition unit 2300 illustrated in FIG. 14 are constituted by the CPU 111, a program stored in the external storage device 114, and an input device (e.g., the keyboard 117 and the mouse 116) illustrated in FIG. 1. Further, for example, the image acquisition unit 2200 and the result output unit 2700 illustrated in FIG. 14 can be constituted by the CPU 111, a program stored in the main memory 112, and the common bus 118 illustrated in FIG. 1.

The object information acquisition unit 2100 can acquire information that identifies an object (i.e., an eye to be inspected), for example, based on an operator's input via the input device (e.g., the keyboard 117 and the mouse 116). In the present exemplary embodiment, the information that identifies the object (i.e., the eye to be inspected) is, for example, an identification number allocated to each object (i.e., the eye to be inspected). Further, a combination of the identification number allocated to the subject and an identifier that represents the inspection target (e.g., aright eye or a left eye) can be used as another example of the information that can identify the object (i.e., the eye to be inspected). Further, the object information acquisition unit 2100 performs processing for acquiring information relating to the object (i.e., the eye to be inspected) stored in a data server (not illustrated) based on the information that identifies the object (i.e., the eye to be inspected).

In the present exemplary embodiment, the information that identifies the object (i.e., the eye to be inspected) is acquired based on the operator's input via the input device. However, in a case where the tomographic image capturing apparatus 120 stores the information that identifies the object (i.e., the eye to be inspected), the stored information can be acquired from the tomographic image capturing apparatus 120 in addition to a tomographic image.

The image acquisition unit 2200 performs processing for requesting the tomographic image capturing apparatus 120 to transmit a predetermined tomographic image and acquiring the tomographic image transmitted from the tomographic image capturing apparatus 120. In the following description, it is presumed that the tomographic image acquired by the image acquisition unit 2200 is an image of the object (i.e., the eye to be inspected) identified by the object information acquisition unit 2100. It is further presumed that the tomographic image acquired by the image acquisition unit 2200 is accompanied by information of various parameters that relate to capturing of the tomographic image.

The instruction acquisition unit 2300 can acquire a processing instruction from an operator that can be entered via the input device. For example, the instruction acquisition unit 2300 acquires an instruction to perform the above-described analysis processing (i.e., either the "processing to be executed when the retinal pigment epithelium is normal" or the "processing to be executed when the retinal pigment epithelium is abnormal"). Further, the instruction acquisition unit 2300 acquires instructions relating to interruption/termination of the analysis processing, storage of analysis results, and storage place. Then, the instruction acquisition unit 2300 transmits, if necessary, the contents of each acquired instruction to the image processing unit 2500 and the result output unit 2700.

The storage unit 2400 can temporarily store information relating to the object (i.e., the eye to be inspected) acquired by the object information acquisition unit 2100. Further, the storage unit 2400 can temporarily store a tomographic image of the object (i.e., the eye to be inspected) acquired by the image acquisition unit 2200. Further, the storage unit 2400 can temporarily store an analysis result of the tomographic image analyzed by the image processing unit 2500. The above-described data stored in the storage unit 2400 can be transmitted, if necessary, to the image processing unit 2500, the display unit 2600, and the result output unit 2700.

The image processing unit 2500 can input a tomographic image from the storage unit 2400 and can execute analysis processing, based on a predetermined disease, on the input tomographic image according to an instruction acquired from the instruction acquisition unit 2300. The image processing unit 2500 according to the present exemplary embodiment includes, as illustrated in FIG. 14, a layer detection unit 2510, a normal structure estimation unit 2520, and a quantification unit 2530.

The layer detection unit 2510 can perform processing for detecting a predetermined layer that constitutes the object (i.e., the eye to be inspected) (e.g., the inner limiting membrane 1003 and the boundary 1005 of the retinal pigment epithelium illustrated in FIGS. 21A to 21D) from the tomographic image acquired from the storage unit 2400. Further, the layer detection unit 2510 can detect a boundary of the nerve fiber layer (see the portion indicated by 1004 in FIG. 21B) in a case where the "processing to be executed when the retinal pigment epithelium is normal" is instructed. Example contents of the processing to be executed by the layer detection unit 2510 are described below.

Figure 21A:
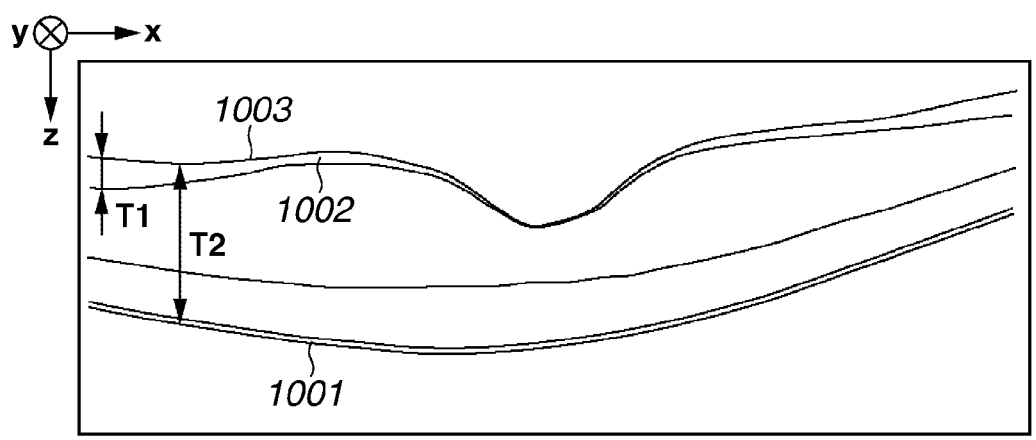
FIGS. 21A, 21B, 21C, and 21D are schematic views illustrating examples of a retinal layer structure of an eye portion that has been captured using the OCT.
Figure 21B:
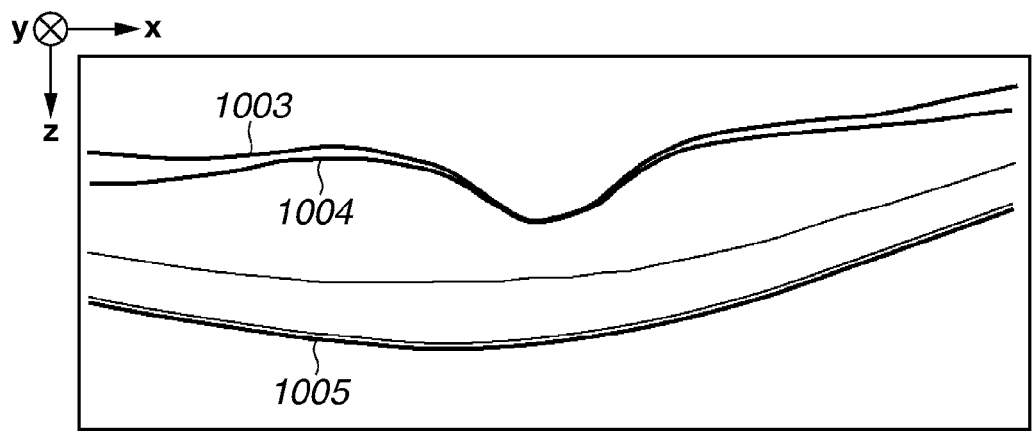
Figure 21C:
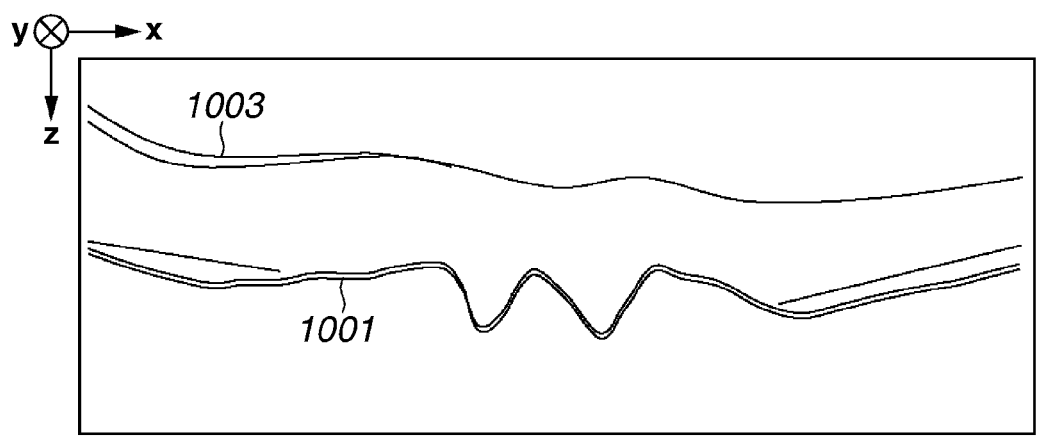
Figure 21D:
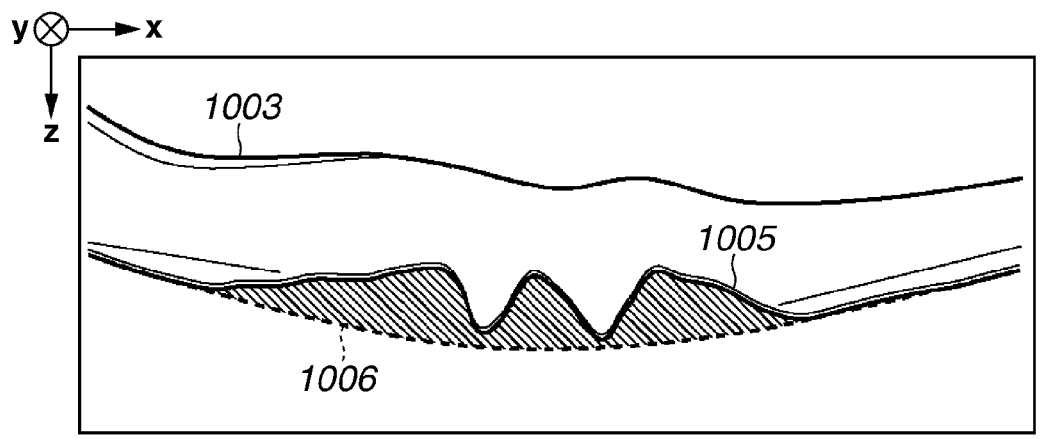

If the "processing to be executed when the retinal pigment epithelium is abnormal" is instructed, the normal structure estimation unit 2520 performs processing for estimating a normal structure of the predetermined layer detected by the layer detection unit 2510 (e.g., a boundary of the retinal pigment epithelium (see the portion indicated by 1006 in FIG. 21D). On the other hand, if the "processing to be executed when the retinal pigment epithelium is normal" is instructed, the normal structure estimation unit 2520 does not perform any processing. Example contents of the processing to be executed by the normal structure estimation unit 2520 are described below.

The quantification unit 2530 can perform processing for quantifying a state of the object (i.e., the eye to be inspected) based on the detection result of the predetermined layer obtained by the layer detection unit 2510 and the normal structure of the predetermined layer estimated by the normal structure estimation unit 2520.

For example, the quantification unit 2530 quantifies the thickness of an entire retinal layer. Further, if the "processing to be executed when the retinal pigment epithelium is normal" is instructed, the quantification unit 2530 quantifies the thickness of the nerve fiber layer (see the portion indicated by 1002 in FIG. 21A). Further, if the "processing to be executed when the retinal pigment epithelium is abnormal" is instructed, the quantification unit 2530 quantifies the difference between a detected boundary of the retinal pigment epithelium and its normal structure (i.e., the turbulence of the retinal pigment epithelium). Example contents of the processing to be executed by the quantification unit 2530 are described below.

The display unit 2600 can display the layer boundary obtained by the image processing unit 2500 together with information relating to its normal structure, on the monitor 115, by superimposing them on the tomographic image. Further, the display unit 2600 can display various numerical data quantified by the quantification unit 2530 on the monitor 115.

The result output unit 2700 can associate inspection date and time, information that identifies the object (i.e., the eye to be inspected), and the tomographic image of the object (i.e., the eye to be inspected) with the analysis result obtained by the image processing unit 2500. Then, the result output unit 2700 transmits the associated data, as information to be stored, to the data server 130.

Next, an example procedure of processing to be executed by the image processing apparatus 110 according to the present exemplary embodiment is described below with reference to FIG. 15.

Figure 15:
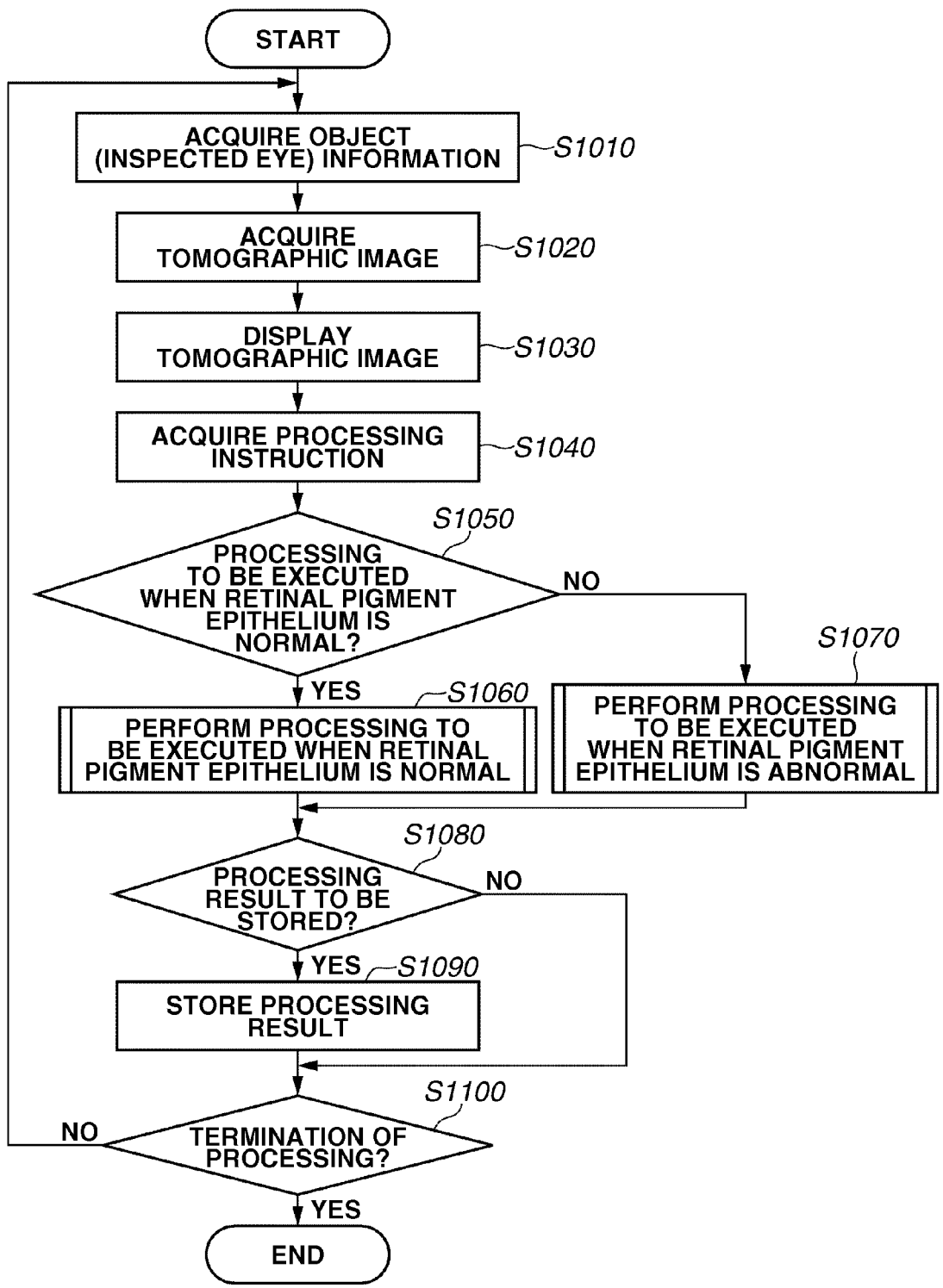
FIG. 15 is a flowchart illustrating an example of a processing procedure of a method for controlling an image processing apparatus according to the fourth exemplary embodiment of the present invention.

FIG. 15 is a flowchart illustrating an example of a processing procedure of a method for controlling the image processing apparatus 110 according to the fourth exemplary embodiment of the present invention. The functional configuration of the image processing apparatus 110 according to the present exemplary embodiment illustrated in FIG. 14 can be realized by the CPU 111 when the CPU 111 executes the program that can realize the functional configuration and controls various operations to be performed by the computer. Further, before performing the following processing, a program code that corresponds to the flowchart illustrated in FIG. 15 is already loaded, for example, from the external storage device 114 to the RAM 112.

First, in step S1010, the object information acquisition unit 2100 acquires information that identifies the object (i.e., the eye to be inspected) from an external source. More specifically, the object information acquisition unit 2100 acquires the information that identifies the object (i.e., the eye to be inspected), for example, from an operator's input via the input device (e.g., the keyboard 117 and the mouse 116). Then, based on the acquired information that identifies the object (i.e., the eye to be inspected), the object information acquisition unit 2100 performs processing for acquiring information relating to the object (i.e., the eye to be inspected) from the data server 130.

For example, the object information acquisition unit 2100 acquires a previously captured tomographic image of the eye to be inspected together with its analysis result (e.g., a layer boundary and quantified numerical data). In particular, if the data server 130 stores normal state data of the boundary of the retinal pigment epithelium that relates to the eye to be inspected, the object information acquisition unit 2100 acquires the stored data from the data server 130. Then, the object information acquisition unit 2100 transmits the acquired information to the storage unit 2400.

Subsequently, in step S1020, the image acquisition unit 2200 performs processing for requesting the tomographic image capturing apparatus 120 to transmit a predetermined tomographic image and acquiring the tomographic image transmitted from the tomographic image capturing apparatus 120. Then, the image acquisition unit 2200 transmits the acquired tomographic image to the storage unit 2400.

Subsequently, in step S1030, the display unit 2600 performs processing for displaying the tomographic image acquired in step S1020 in the monitor 115. In the present exemplary embodiment, for example, the image schematically illustrated in FIG. 21A or FIG. 21C can be displayed on the monitor 115. In the present exemplary embodiment, the tomographic image is three-dimensional data. Therefore, the image actually displayed on the monitor 115 is a two-dimensional tomographic image (i.e., a clipped image) that is obtainable by cutting the three-dimensional image along a target cross section. It is desired that the cross section to be displayed is arbitrarily selectable via a graphical user interface (GUI). Further, it is also useful to display various past data (e.g., the tomographic image and its analysis result) acquired in step S1010 in an appropriately arrayed manner.

Subsequently, in step S1040, the instruction acquisition unit 2300 acquires a processing instruction input by an operator via the input device (e.g., the keyboard 117 and the mouse 116). More specifically, in the present exemplary embodiment, the instruction acquisition unit 2300 acquires an instruction to perform the "processing to be executed when the retinal pigment epithelium is normal" or the "processing to be executed when the retinal pigment epithelium is abnormal." In this case, an operator determines the analysis processing to be executed by the image processing apparatus 110 and inputs a determination result (i.e., selected processing) to the image processing apparatus 110. Then, the processing instruction obtained in step S1040 is transmitted to the image processing unit 2500.

Subsequently, in step S1050, for example, the image processing unit 2500 determines whether the processing instruction obtained in step S1040 is the "processing to be executed when the retinal pigment epithelium is normal."

As a result of the determination in step S1050, if it is determined that the processing instruction obtained in step S1040 is the "processing to be executed when the retinal pigment epithelium is normal", the processing proceeds to step S1060. On the other hand, as a result of the determination in step S1050, if it is determined that the processing instruction obtained in step S1040 is not the "processing to be executed when the retinal pigment epithelium is normal" (i.e., when the processing instruction obtained in step S1040 is the "processing to be executed when the retinal pigment epithelium is abnormal"), the processing proceeds to step S1070.

When the processing proceeds to step S1060, the image processing unit 2500 executes analysis processing relating to the "processing to be executed when the retinal pigment epithelium is normal." Further, the display unit 2600 performs processing for displaying a result of the analysis processing performed by the image processing unit 2500. Example processing to be executed in step S1060 is described below in detail with reference to a flowchart illustrated in FIG. 16. Subsequently, the processing proceeds to step S1080.

On the other hand, when the processing proceeds to step S1070, the image processing unit 2500 executes analysis processing relating to the "processing to be executed when the retinal pigment epithelium is abnormal." Further, the display unit 2600 performs processing for displaying a result of the analysis processing performed by the image processing unit 2500. Example processing to be executed in step S1070 is described below in detail with reference to a flowchart illustrated in FIG. 17. Subsequently, the processing proceeds to step S1080.

When the processing proceeds to step S1080, first, the instruction acquisition unit 2300 performs processing for acquiring an instruction input from an operator, for example, via the keyboard 117 or the mouse 116, to determine whether to store the present processing result relating to the object (i.e., the eye to be inspected) in the data server 130. Then, for example, the result output unit 2700 determines whether to store the present processing result relating to the object (i.e., the eye to be inspected) in the data server 130 according to the instruction acquired by the instruction acquisition unit 2300.

As a result of the determination in step S1080, if it is determined that the present processing result relating to the object (i.e., the eye to be inspected) is to be stored in the data server 130, the processing proceeds to step S1090. On the other hand, as a result of the determination in step S1080, if it is determined that the present processing result relating to the object (i.e., the eye to be inspected) is not to be stored in the data server 130, the processing proceeds to step S1100.

When the processing proceeds to step S1090, the result output unit 2700 associates the inspection date and time, the information that identifies the object (i.e., the eye to be inspected), the tomographic image of the object (i.e., the eye to be inspected) with the analysis result obtained by the image processing unit 2500. Then, the result output unit 2700 transmits the associated data, as information to be stored, to the data server 130. Subsequently, the processing proceeds to step S1100.

When the processing proceeds to step S1100, the instruction acquisition unit 2300 performs processing for acquiring an instruction that is, for example, input from an operator via the keyboard 117 or the mouse 116 to instruct whether to terminate the tomographic image analysis processing to be performed by the image processing apparatus 110. Then, the image processing apparatus 110 determines whether to terminate the tomographic image analysis processing according to the instruction acquired by the instruction acquisition unit 2300.

As a result of the determination in step S1100, if the image processing apparatus 110 does not terminate the tomographic image analysis processing, the processing returns to step S1010. Processing on the next object (i.e., the eye to be inspected), or re-processing on the same eye to be inspected, is executed. On the other hand, as a result of the determination in step S1100, if it is determined that the image processing apparatus 110 terminates the tomographic image analysis processing, the image processing apparatus 110 terminates the processing of the flowchart illustrated in FIG. 15.

Next, a detailed processing procedure of the processing to be executed in step S1060 illustrated in FIG. 15 is described below with reference to FIG. 16.

Figure 16:
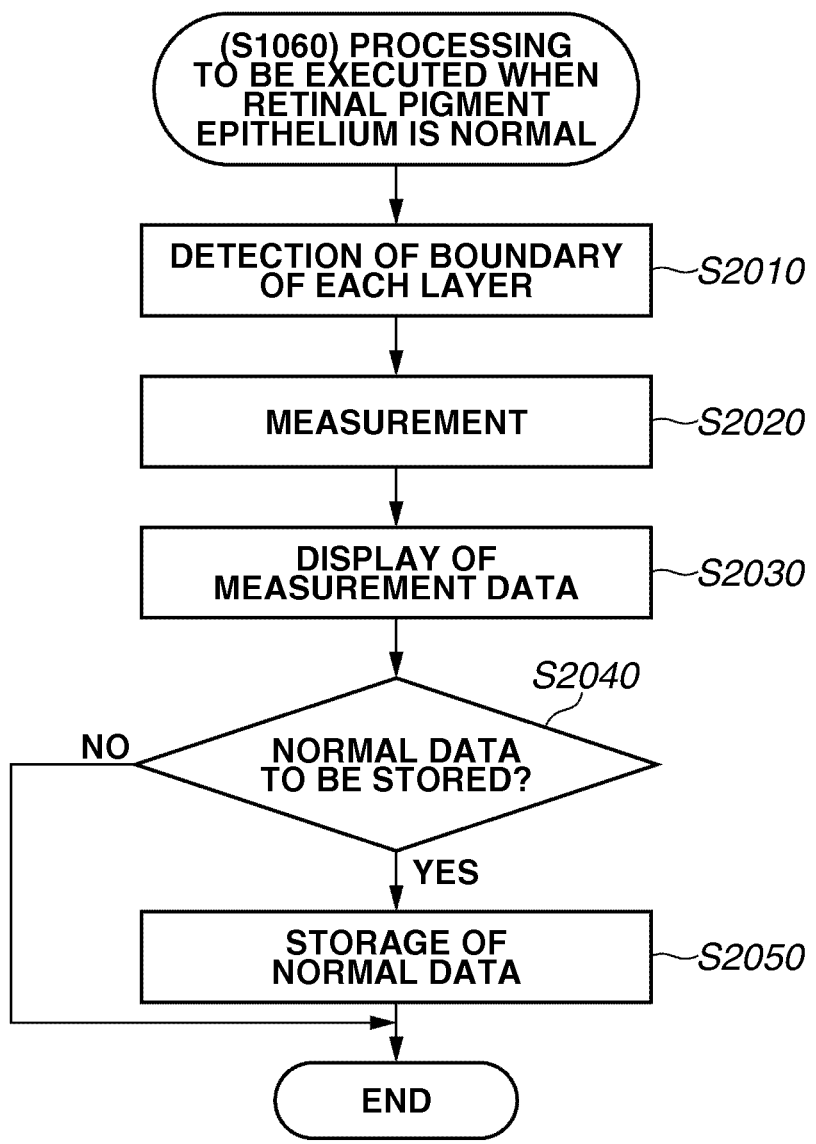
FIG. 16 is a flowchart illustrating an example of a detailed processing procedure of "processing to be executed when the retinal pigment epithelium is normal" to be performed in step S1060 illustrated in FIG. 15.

FIG. 16 is a flowchart illustrating an example of the detailed processing procedure of the "processing to be executed when the retinal pigment epithelium is normal", to be executed in step S1060 illustrated in FIG. 15.

First, in step S2010, the layer detection unit 2510 performs processing for acquiring a tomographic image of the object (i.e., the eye to be inspected) from the storage unit 2400 and detecting a predetermined layer that constitutes the object (i.e., the eye to be inspected) from the acquired tomographic image. More specifically, the layer detection unit 2510 detects the inner limiting membrane 1003, the boundary 1004 of the nerve fiber layer, and the boundary 1005 of the retinal pigment epithelium illustrated in FIGS. 21A to 21D, from the tomographic image of the object (i.e., the eye to be inspected). Further, the layer detection unit 2510 detects coordinate data of a fovea centralis that is the center of the macula lutea portion. Then, the layer detection unit 2510 outputs the detection results to the storage unit 2400.

An example processing method for detecting a layer boundary, which can be executed by the layer detection unit 2510, is described below. In the present exemplary embodiment, a three-dimensional tomographic image serving as a processing target is regarded as an assembly of two-dimensional tomographic images (B-scan images) and the following two-dimensional image processing is executed on each two-dimensional tomographic image.

First, the layer detection unit 2510 performs smoothing filter processing on the target two-dimensional tomographic image to remove noise components. Then, the layer detection unit 2510 detects edge components from the tomographic image and extracts some line segments as layer boundary candidates based on a connected state of them. Then, the layer detection unit 2510 selects the uppermost line segment, from these candidates, as the inner limiting membrane 1003. Further, the layer detection unit 2510 selects a line segment beneath the inner limiting membrane 1003 as the boundary 1004 of the nerve fiber layer. Further, the layer detection unit 2510 selects the lowermost line segment as the boundary 1005 of the retinal pigment epithelium.

Further, the detection accuracy can be improved by applying an appropriate dynamic contour method (e.g., Snakes or level set method) to these line segments being set as initial values. Further, the GraphCut method can be used to detect the layer boundary.

The above-described dynamic contour method or the GraphCut based boundary detection method can be three-dimensionally applied to a three-dimensional tomographic image. Alternatively, when an input three-dimensional tomographic image (i.e., processing target) is regarded as an assembly of two-dimensional tomographic images, the above-described method can be two-dimensionally applied to each two-dimensional tomographic image. Further, the layer boundary detection method is not limited to the above-described methods. Any other method is usable if a boundary of a layer can be detected from a tomographic image of an eye portion.

The layer detection unit 2510 further detects coordinate data of the fovea centralis, using the inner limiting membrane 1003. More specifically, the layer detection unit 2510 identifies a point where the z-coordinate of the detected inner limiting membrane 1003 is maximized in the vicinity of the tomographic image as the fovea centralis. A coordinate system having an origin at the fovea centralis is employed for the following processing. To this end, all coordinates are converted (horizontally moved).

Subsequently, in step S2020, the quantification unit 2530 measures a thickness of the nerve fiber layer 1002 and an overall thickness of the retinal layer, based on the layer boundary detected in step S2010, to perform quantification of necessary information.

First, the quantification unit 2530 measures the thickness (see T1 illustrated in FIG. 21A) of the nerve fiber layer 1002 by obtaining a z-coordinate difference between the boundary 1004 of the nerve fiber layer and the inner limiting membrane 1003, at each coordinate point on the x-y plane. Similarly, the quantification unit 2530 measures the overall thickness (T2 illustrated in FIG. 21A) of the retinal layer by obtaining a z-coordinate difference between the boundary 1005 of the retinal pigment epithelium and the inner limiting membrane 1003. Further, the quantification unit 2530 measures a cross-sectional area of each layer (nerve fiber layer 1002 and the entire retinal layer) by adding layer thicknesses at respective coordinate points in the x-axis direction for each y-coordinate. Further, the quantification unit 2530 measures a volume of each layer by adding obtained areas in the y-axis direction. Then, the quantification unit 2530 outputs the data relating to the measurement results to the storage unit 2400.

Subsequently, in step S2030, the display unit 2600 performs processing for superimposing the layer boundary detection result obtained in step S2010 on the tomographic image and displaying the superimposed image on the monitor 115. For example, in a case where each layer boundary is expressed with a line (see FIG. 21B), it is desired to use a predetermined color line for each boundary. For example, the display unit 2600 can use a red line for the inner limiting membrane 1003, a yellow line for the boundary 1004 of the nerve fiber layer, and a green line for the boundary 1005 of the retinal pigment epithelium.

Further, for example, the display unit 2600 can use a semi-transparent color to display (present) the region of each layer without explicitly indicating layer boundaries. For example, the display unit 2600 can use a red color to indicate the area of the nerve fiber layer 1002 and a green to indicate the rest of the retinal layer. It is desired that a desirable color is arbitrarily selectable via the GUI to indicate a target cross section. Further, the conventionally known volume rendering technique can be employed to realize a three-dimensional display.

Further, the display unit 2600 performs processing for displaying information relating to the layer thicknesses measured through the quantification in step S2020 on the monitor 115. For example, the display unit 2600 can display a distribution map of layer thicknesses relative to the entire three-dimensional tomographic image (i.e., the x-y plane). Alternatively, the display unit 2600 can display the area of each layer in a target cross section in association with the above-described display of the detection result. Further, the display unit 2600 can display an overall volume, or can display a volume of a limited region calculated according to a designation of an operator on the x-y plane.

Subsequently, in step S2040, first, the instruction acquisition unit 2300 performs processing for acquiring an instruction whether to store a group of coordinate points that represent the boundary 1005 of the retinal pigment epithelium detected in step S2010 as normal state data representing the boundary of the retinal pigment epithelium of the object (i.e., the eye to be inspected). For example, an operator can input the instruction via the keyboard 117 or the mouse 116. Then, for example, the result output unit 2700 determines whether to store the group of coordinate points that represent the boundary 1005 of the retinal pigment epithelium detected in step S2010 as normal state data representing a boundary of the retinal pigment epithelium of the object (i.e., the eye to be inspected) according to the instruction acquired by the instruction acquisition unit 2300.

As a result of the determination in step S2040, if it is determined that the group of coordinate points that represent the boundary 1005 of the retinal pigment epithelium detected in step S2010 is not stored as normal state data representing the boundary of the retinal pigment epithelium of the object (i.e., the eye to be inspected), the image processing apparatus 110 terminates the processing of the flowchart illustrated in FIG. 16. On the other hand, as a result of the determination in step S2040, if it is determined that the group of coordinate points that represent the boundary 1005 of the retinal pigment epithelium detected in step S2010 is stored as normal state data representing the boundary of the retinal pigment epithelium of the object (i.e., the eye to be inspected), the processing proceeds to step S2050.

When the processing proceeds to step S2050, the result output unit 2700 transmits the boundary data of the retinal pigment epithelium detected in step S2010 (i.e., the group of coordinate points that represent the layer boundary), as normal state data representing the boundary of the retinal pigment epithelium of the object (i.e., the eye to be inspected), to the data server 130. Therefore, the data server 130 can store the data acquired from the result output unit 2700 in association with the object (i.e., the eye to be inspected), as normal state data representing the boundary of the retinal pigment epithelium. Subsequently, the image processing apparatus 110 terminates the processing of the flowchart illustrated in FIG. 16 (i.e., the processing of step S1060 illustrated in FIG. 15).

In the present exemplary embodiment, only the thicknesses of the nerve fiber layer 1002 and the entire retinal layer are measured in the processing of step S1060. However, it is also useful to analyze other layers, such as a photoreceptor layer and an outer limiting membrane, of the eye portion.

Next, a detailed processing procedure of the processing to be executed in step S1070 of FIG. 15 is described below with reference to FIG. 17.

Figure 17:
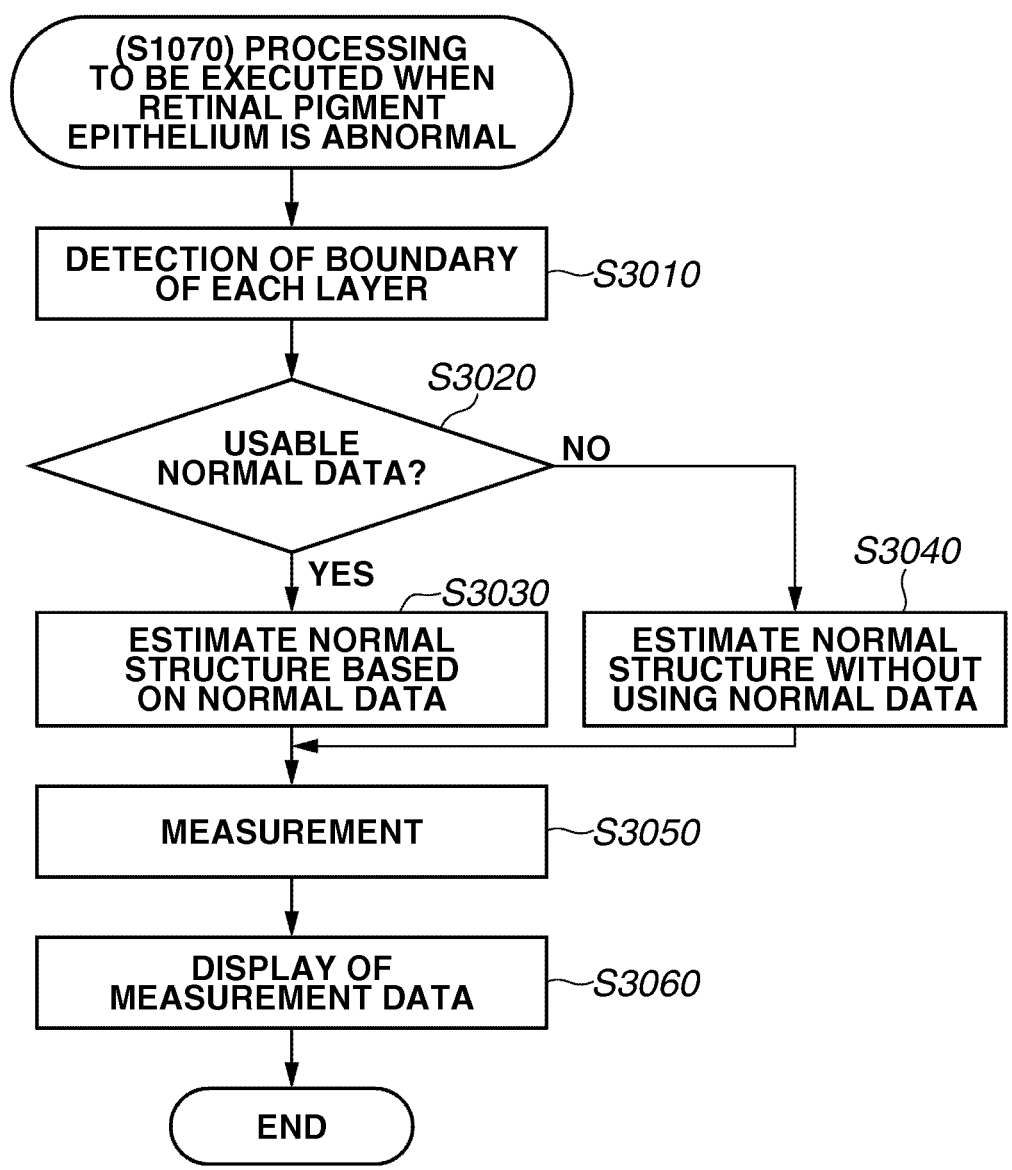
FIG. 17 is a flowchart illustrating an example of a detailed processing procedure of "processing to be executed when the retinal pigment epithelium is abnormal" to be performed in step S1070 illustrated in FIG. 15.

FIG. 17 is a flowchart illustrating an example of the detailed processing procedure of the "processing to be executed when the retinal pigment epithelium is abnormal" illustrated in step S1070 of FIG. 15.

First, in step S3010, the layer detection unit 2510 performs processing for acquiring a tomographic image of the object (i.e., the eye to be inspected) from the storage unit 2400 and detecting a predetermined layer that constitutes the object (i.e., the eye to be inspected) from the acquired tomographic image. More specifically, the layer detection unit 2510 detects the inner limiting membrane 1003 and the boundary 1005 of the retinal pigment epithelium (see FIGS. 21A to 21D) from the tomographic image of the object (i.e., the eye to be inspected). Further, the layer detection unit 2510 detects coordinate data of a fovea centralis that is the center of the macula lutea portion. Then, the layer detection unit 2510 outputs the detection results to the storage unit 2400.

In the present exemplary embodiment, the layer detection unit 2510 can use an appropriate layer boundary detection method that can be similar to that described in step S2010 although its detailed description is not repeated. A coordinate system having an origin at the fovea centralis is employed for the following processing. To this end, all coordinates are converted (horizontally moved).

Subsequently, in step S3020, the normal structure estimation unit 2520 determines whether the normal state data representing the boundary of the retinal pigment epithelium of the object (i.e., the eye to be inspected) is usable, referring to the information relating to the object (i.e., the eye to be inspected) acquired by the object information acquisition unit 2100 in step S1010. More specifically, to determine the usability in step S3020, the normal structure estimation unit 2520 checks whether the normal state data representing the boundary of the retinal pigment epithelium of the object (i.e., the eye to be inspected) is included in the information relating to the object (i.e., the eye to be inspected) acquired by the object information acquisition unit 2100 in step S1010.

As a result of the determination in step S3020, if it is determined that the normal state data representing the boundary of the retinal pigment epithelium of the object (i.e., the eye to be inspected) is usable, the normal structure estimation unit 2520 acquires the normal state data from the storage unit 2400. Subsequently, the processing proceeds to step S3030. On the other hand, as a result of the determination in step S3020, if it is determined that the normal state data representing the boundary of the retinal pigment epithelium of the object (i.e., the eye to be inspected) is unusable, the display unit 2600 performs a display informing that the normal state data is unusable. Subsequently, the processing proceeds to step S3040.

When the processing proceeds to step S3030, the normal structure estimation unit 2520 performs processing for estimating a normal structure of the boundary of the retinal pigment epithelium on the tomographic image by performing processing for applying the normal state data representing the boundary of the retinal pigment epithelium acquired in step S3020 to the tomographic image. Then, after terminating the processing of step S3030, the processing proceeds to step S3050.

An example processing method for estimating a normal structure of the boundary of the retinal pigment epithelium in step S3030 is described below.

The normal state data is expressed using a coordinate system setting an origin at the fovea centralis on the tomographic image when the data is acquired. On the other hand, the tomographic image (i.e., present tomographic image) acquired in step S1020 is expressed using a coordinate system (i.e., present coordinate system) having an origin at its fovea centralis. Hence, the normal structure estimation unit 2520 performs processing for overlapping the normal state data with the present coordinate system so that these coordinate systems coincide with each other. Then, the normal structure estimation unit 2520 designates the overlapped normal state data as initial normal structure of the boundary of the retinal pigment epithelium on the present tomographic image. Namely, the normal structure estimation unit 2520 performs initial alignment.

Then, the normal structure estimation unit 2520 updates the normal structure by performing application processing to the boundary 1005 of the retinal pigment epithelium detected on the present tomographic image. In other words, the normal structure estimation unit 2520 defines an initial value of a conversion matrix A for converting the normal state data into a normal structure as a unit matrix, and estimates a conversion matrix A that can obtain an appropriate normal structure. In the present exemplary embodiment, the conversion matrix A is defined as a matrix that represents a three-dimensional rigid conversion, a matrix that includes deformation of a uniform scale, or a matrix that allows overall affine conversion.

In the present exemplary embodiment, to execute the above-described application processing, a difference $\epsilon_i$ between a detection result and a normal structure is defined according to the above-described formula (1).

In the formula (1), Xorg_i represents coordinate data of an i-th point of the normal state data described as a group of coordinate points. Further, in the formula (1), Xnormal_i represents coordinate data of a point obtained through the coordinate conversion using the conversion matrix A (i.e., point on the normal structure). Further, in the formula (1), Xdetected_i represents coordinate data of a point on the boundary 1005 of the retinal pigment epithelium corresponding to the Xnormal_i. The above-described associating processing can be performed by selecting a point on the boundary 1005 of the retinal pigment epithelium, for example, by selecting a point on the boundary 1005 of the retinal pigment epithelium that is identical in x and y coordinates to the Xnormal_i or that is closest to the Xnormal_i. In the formula (1), the coordinate data and the coordinate conversion matrix are expressed using the same-order coordinate system.

Then, the normal structure estimation unit 2520 obtains a conversion matrix A that minimizes the evaluation formula expressed using the above-described formula (2). In the formula (2), $\rho(x)$ is a weighting function. FIGS. 6A to 6C are schematic views illustrating examples of the weighting function that can be used to estimate a normal structure of the above-described layer included in the tomographic image.

In FIGS. 6A, 6B, and 6C, the abscissa axis represents x (that takes 0 at the center) and the ordinate axis represents the weighting function $\rho(x)$. The weighting function to be used in the above-described estimation of the normal structure of the layer included in the tomographic image is not limited to the examples illustrated in FIGS. 6A, 6B, and 6C. Any other function can be set. Further, minimizing the formula (2) is equivalent to obtaining the conversion matrix A using the least squares method or the M estimation method.

On the other hand, when the processing proceeds to step S3040, the normal structure estimation unit 2520 performs processing for estimating a normal structure by applying a polynomial curve to the boundary 1005 of the retinal pigment epithelium on each two-dimensional cross section of the tomographic image. The above-described estimation processing method is similar to the method described in the background technique. Subsequently, the processing proceeds to step S3050.

When the processing proceeds to step S3050, the quantification unit 2530 measures a thickness of the entire retinal layer based on the layer boundaries detected in step S3010 and quantifies the measured thickness. Further, the quantification unit 2530 performs processing for quantifying a turbulence of the retinal pigment epithelium 1001 based on a difference between the boundary 1005 of the retinal pigment epithelium detected in step S3010 and its normal structure 1006 estimated in step S3030 or in step S3040. Then, the quantification unit 2530 outputs these measurement results to the storage unit 2400.

The processing for quantifying the thickness of the entire retinal layer is similar to the processing performed in step S2020 although its detailed description is not repeated. Further, regarding the processing for quantifying the turbulence of the retinal pigment epithelium 1001, the quantification with respect to the thickness, area, and volume of a different portion is similar to the above-described layer thickness quantification although its detailed description is not repeated.

Further, the feature quantity that represents the turbulence of the retinal pigment epithelium 1001 can be any value obtainable by quantifying the difference between the boundary 1005 of the retinal pigment epithelium detected in step S3010 and its normal structure 1006. For example, a distribution, a maximum value, an average value, a central value, a variance, or a standard deviation of the obtained difference (thickness), or any other value (e.g., the number (or ratio) of points that are equal to or greater than a threshold) can be obtained and used as a feature quantity that represents an area caused by the difference. Further, a density histogram, an average density value, a density variance value, or a contrast value can be obtained as the feature quantity that represents the area caused by the difference.

Subsequently, in step S3060, the display unit 2600 performs processing for displaying the boundary 1005 of the retinal pigment epithelium detected in step S3010 and its normal structure 1006 estimated in step S3030 or in step S3040 that are superimposed on the tomographic image. Further, the display unit 2600 performs processing for displaying the measurement data quantified in step S3050 in addition to the above-described superimposed image. The above-described display processing is similar to the processing to be executed in step S2030 although its detailed description is not repeated.

Upon completing the processing of step S3060, the image processing apparatus 110 terminates the processing of the flowchart illustrated in FIG. 17 (i.e., the processing of step S1070 illustrated in FIG. 15).

As described above, the fourth exemplary embodiment performs processing for applying a boundary of the retinal pigment epithelium obtained in a normal state of the object itself (i.e., the eye to be inspected). Therefore, the fourth exemplary embodiment can accurately estimate a normal structure of the retinal pigment epithelium that constitutes the object in the tomographic image.

Accordingly, the fourth exemplary embodiment can accurately quantify a state (e.g., turbulence in shape) of the retinal pigment epithelium. Therefore, the fourth exemplary embodiment can quantitatively analyze, for example, the stage of a disease (e.g., age-related macular degeneration) or the degree of recovery from the disease after treatment. Further, the fourth exemplary embodiment can accurately detect a predetermined layer that constitutes the object even when a boundary of the predetermined layer cannot be partly observed on the tomographic image.

Next, a fifth exemplary embodiment of the present invention is described below in detail. As described above, the image processing apparatus 110-4 according to the fourth exemplary embodiment is configured to acquire a tomographic image of the object (i.e., the eye to be inspected), which has been captured by the tomographic image capturing apparatus 120, execute analysis processing, based on a predetermined disease, on the acquired image according to an operator's instruction, and quantify the disease. An image processing apparatus according to the fifth exemplary embodiment is similar to the image processing apparatus described in the fourth exemplary embodiment in that the analysis processing is performed on the acquired tomographic image of the object (i.e., the eye to be inspected).

However, the image processing apparatus according to the fifth exemplary embodiment is different from the image processing apparatus described in the fourth exemplary embodiment in that the processing for determining whether to execute the "processing to be executed when the retinal pigment epithelium is normal" or the "processing to be executed when the retinal pigment epithelium is abnormal" is automatically performed without relying on an operator's instruction.

Figure 18:
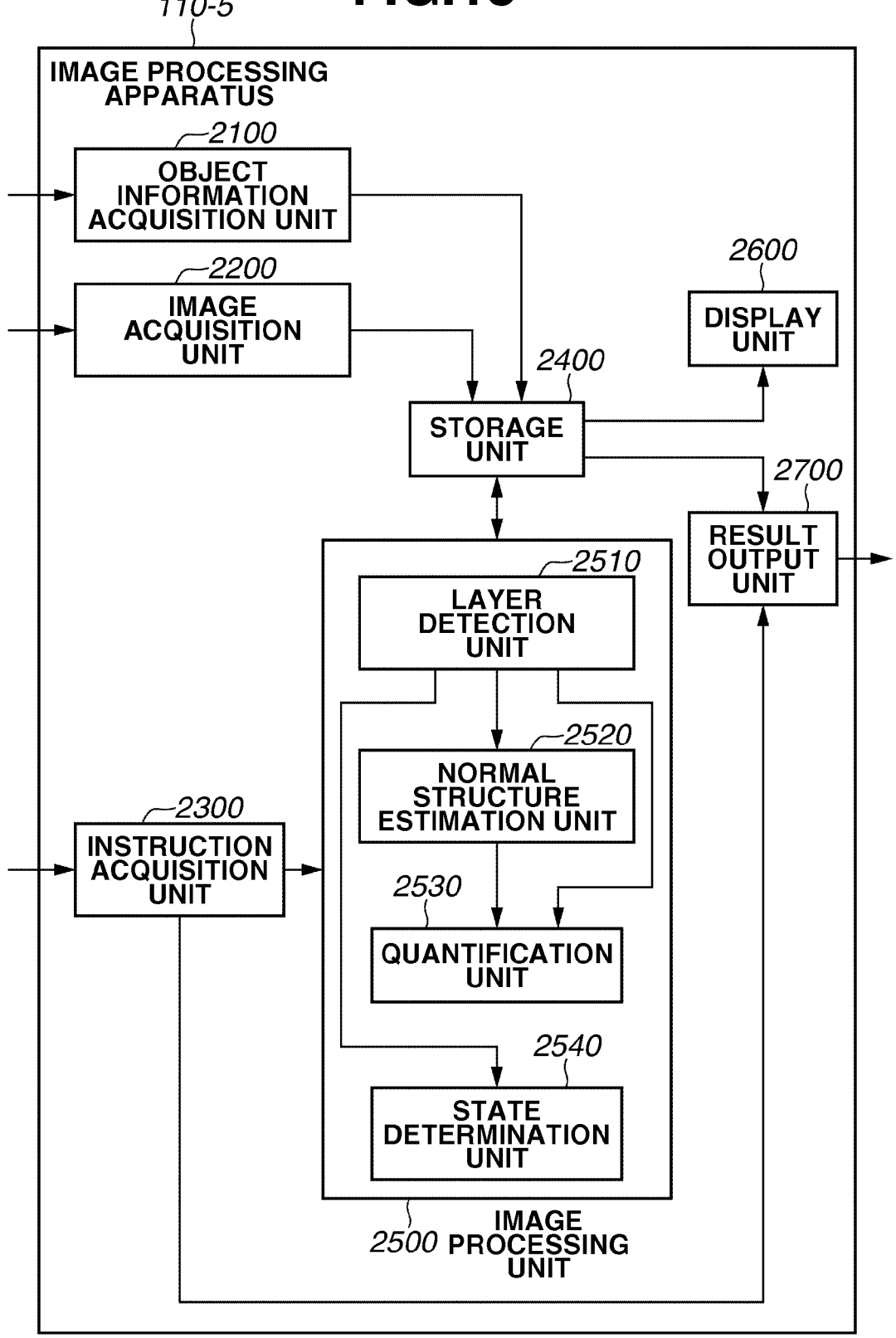
FIG. 18 is a schematic view illustrating an example of a functional configuration of an image processing apparatus according to a fifth exemplary embodiment of the present invention.

FIG. 18 is a schematic view illustrating an example of a functional configuration of the image processing apparatus 110 according to the fifth exemplary embodiment of the present invention. In FIG. 18, constituent components similar to those illustrated in FIG. 14 are denoted by the same reference numerals. As illustrated in FIG. 18, the image processing apparatus 110-5 according to the fifth exemplary embodiment is different from the image processing apparatus 110-4 described in the fourth exemplary embodiment (see FIG. 14) in the functional configuration in which a state determination unit 2540 is additionally provided in the image processing unit 2500. The following description is mainly given for characteristic features of the present exemplary embodiment that are not described in the fourth exemplary embodiment.

The state determination unit 2540 determines whether the retinal pigment epithelium is normal or abnormal based on the boundary 1005 of the retinal pigment epithelium detected by the layer detection unit 2510. Example processing to be executed by the state determination unit 2540 is described below.

Next, an example procedure of the processing to be executed by the image processing apparatus 110-5 according to the present exemplary embodiment is described below with reference to FIG. 19.

Figure 19:
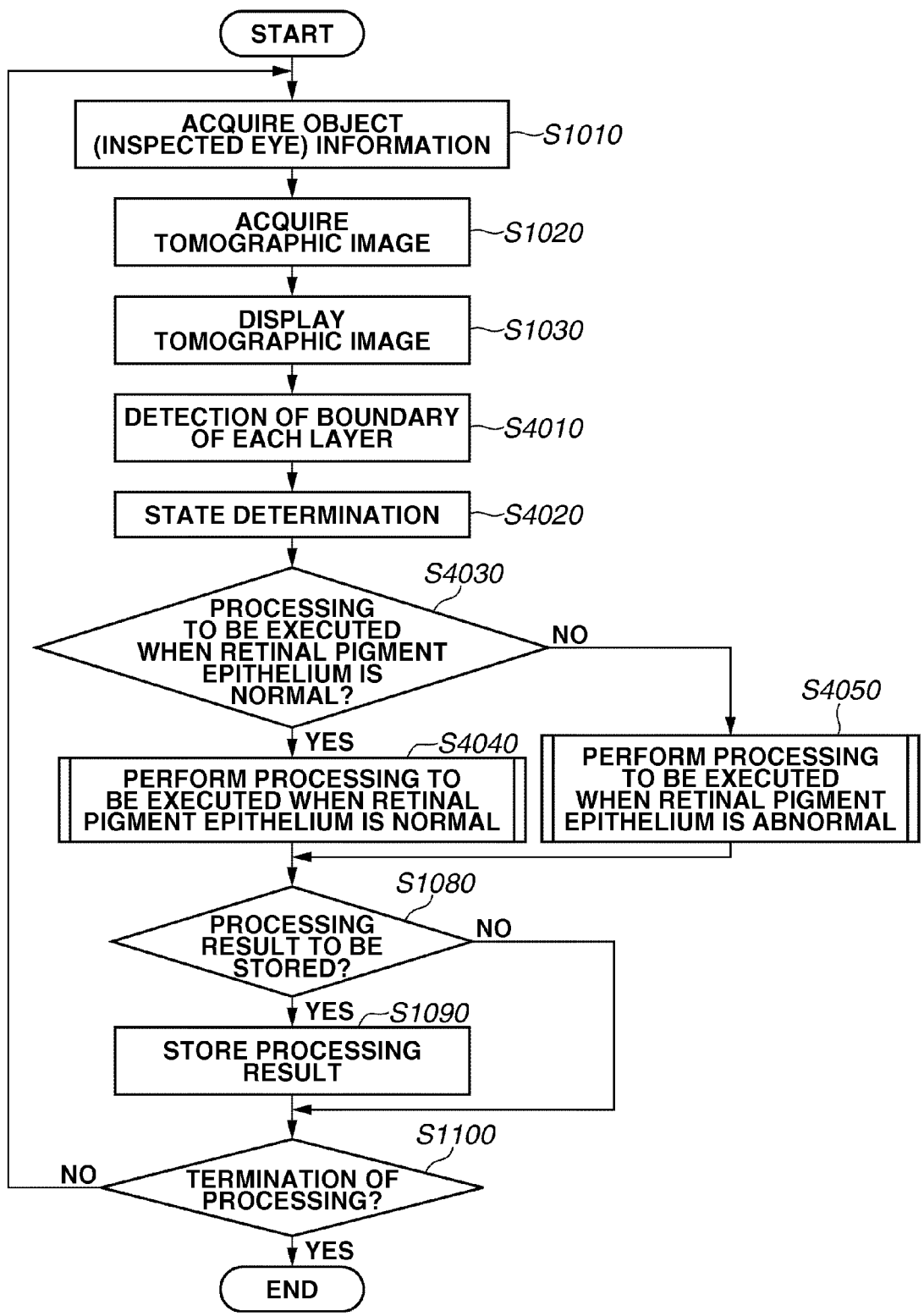
FIG. 19 is a flowchart illustrating an example of a processing procedure of a method for controlling an image processing apparatus according to the fifth exemplary embodiment of the present invention.
Figure 20A:
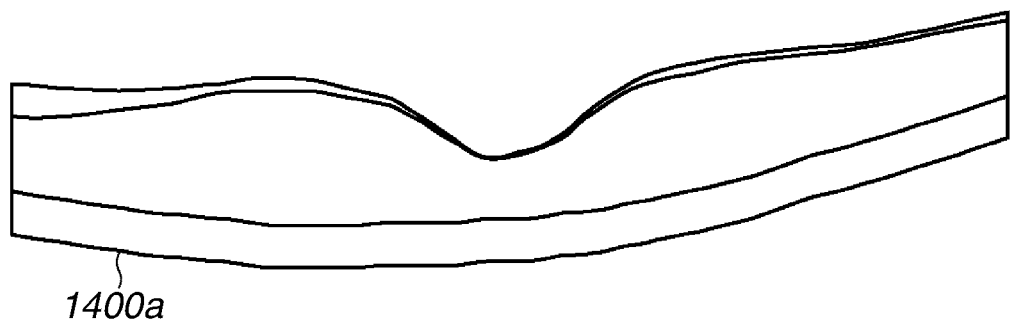
FIGS. 20A, 20B and 20C are schematic views illustrating examples of the general retinal layer structure.
Figure 20B:
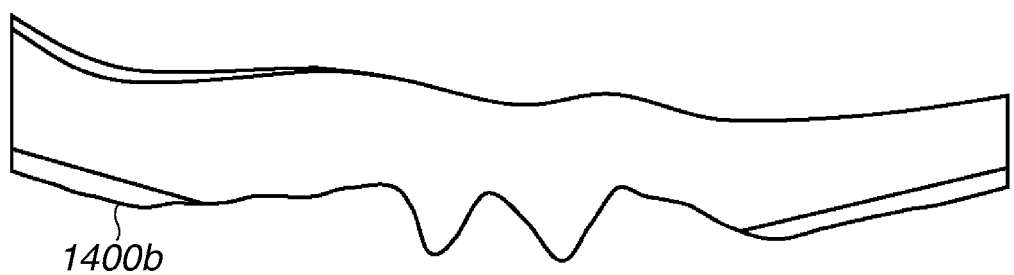
Figure 20C:
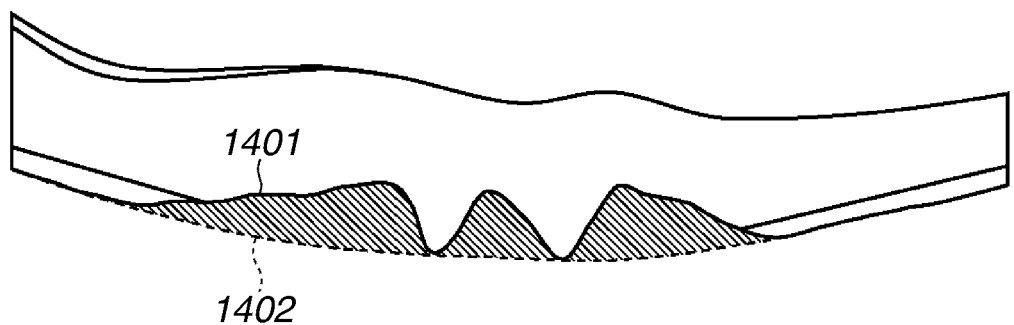

FIG. 19 is a flowchart illustrating an example of a processing procedure of a method for controlling the image processing apparatus 110 according to the fifth exemplary embodiment of the present invention. Steps in FIG. 19 are denoted by the step numbers used in FIG. 15 if the processing to be performed in these steps is similar to those in the above-described fourth exemplary embodiment, and their detailed descriptions are not repeated.

First, the image processing apparatus 110 according to the fifth exemplary embodiment performs processing that is similar to the above-described processing of steps S1010 to S1030 illustrated in FIG. 15.

Subsequently, in step S4010, the layer detection unit 2510 performs processing for acquiring a tomographic image of the object (i.e., the eye to be inspected) from the storage unit 2400 and detecting a predetermined layer that constitutes the object (i.e., the eye to be inspected) from the acquired tomographic image. More specifically, the layer detection unit 2510 detects the inner limiting membrane 1003, the boundary 1004 of the nerve fiber layer, and the boundary 1005 of the retinal pigment epithelium (see FIGS. 21A to 21D) from the tomographic image of the object (i.e., the eye to be inspected). Then, the layer detection unit 2510 outputs the detection results to the storage unit 2400. The processing to be performed in step S4010 is similar to the processing described in the fourth exemplary embodiment (see step S2010 illustrated in FIG. 16) and accordingly its detailed descriptions is not repeated.

Subsequently, in step S4020, the state determination unit 2540 determines whether the retinal pigment epithelium is normal, referring to the boundary 1005 of the retinal pigment epithelium detected in step S4010. For example, if a maximum curvature of the boundary 1005 of the retinal pigment epithelium detected in step S4010 is equal to or greater than a predetermined threshold, the state determination unit 2540 determines that the retinal pigment epithelium is abnormal. Then, the state determination unit 2540 outputs the determination result to the storage unit 2400.

Any other method can be used in step S4020 to determine whether the retinal pigment epithelium is normal. For example, to determine the normality of the retinal pigment epithelium in step S4020, the state determination unit 2540 can check whether the number of local maximums and local minimums with respect to the boundary 1005 of the retinal pigment epithelium is equal to or greater than a threshold. Further, the number of inflection points can be referred to in the above-described determination. Similarly, the variance of the curvature can be referred to in the above-described determination.

Further, for example, to determine the normality of the retinal pigment epithelium in step S4020, the state determination unit 2540 can perform principal component analysis on a group of three-dimensional coordinate points that represent the boundary 1005 of the retinal pigment epithelium and determine whether the third principal component that represents a dispersion in the z-axis direction is equal to or greater than a threshold. Further, it is useful to perform frequency analysis based on the Fourier transformation to use the intensity of a predetermined frequency range for the above-described determination. The above-described processing can be performed on only a limited part of the boundary 1005, such as the vicinity of the fovea centralis, where abnormality tends to be recognized.

Subsequently, in step S4030, for example, the image processing unit 2500 determines whether to perform the "processing to be executed when the retinal pigment epithelium is normal" based on the determination result obtained in the processing of step S4020.

As a result of the determination in step S4030, if it is determined that the "processing to be executed when the retinal pigment epithelium is normal" is to be performed (i.e., when the determination result in the processing of step S4020 is that the retinal pigment epithelium is normal), the processing proceeds to step S4040. On the other hand, as a result of the determination in step S4030, if it is determined that the "processing to be executed when the retinal pigment epithelium is normal" is not to be performed (i.e., when the determination result obtained in the processing of step S4020 is that the retinal pigment epithelium is abnormal), the processing proceeds to step S4050.

When the processing proceeds to step S4040, the image processing unit 2500 executes analysis processing relating to the "processing to be executed when the retinal pigment epithelium is normal." Detailed contents of the processing to be performed in step S4040 are basically similar to those described in the fourth exemplary embodiment (see step S1060 illustrated in FIG. 15. However, in the present exemplary embodiment, the image processing apparatus 110 does not execute the layer boundary detection processing (i.e., the processing of step S2010 illustrated in FIG. 16).

On the other hand, when the processing proceeds to step S4050, the image processing unit 2500 executes analysis processing relating to the "processing to be executed when the retinal pigment epithelium is abnormal." Detailed contents of the processing to be performed in step S4050 are basically similar to those described in the fourth exemplary embodiment (see step S1070 illustrated in FIG. 15. However, in the present exemplary embodiment, the image processing apparatus 110 does not execute the layer boundary detection processing (i.e., the processing of step S3010 illustrated in FIG. 17).

Then, after terminating the processing of step S4040 or step S4050, the processing proceeds to step S1080. The image processing apparatus 110 performs the processing of steps S1080 to S1100 as described in the fourth exemplary embodiment with reference to FIG. 15.

As described above, the image processing apparatus 110 according to the above-described fifth exemplary embodiment determines whether the retinal pigment epithelium of the object (i.e., the eye to be inspected) is normal. Therefore, in addition to the effects of the fourth exemplary embodiment, the fifth exemplary embodiment can automatically store the data as normal state data if it is determined that the data is normal. Therefore, in a case where the retinal pigment epithelium is abnormal, the image processing apparatus 110 can estimate a normal structure of the retinal pigment epithelium based on the normal state data stored beforehand and can quantitatively evaluate its state (e.g., turbulence in shape).

Next, a sixth exemplary embodiment of the present invention is described below referring to some modified examples of the above-described fifth exemplary embodiment. Hereinafter, each modified example is described below.

A first modified example according to the present exemplary embodiment is described below. In the above-described exemplary embodiments, the normal structure estimation unit 2520 estimates a normal structure of a predetermined layer using the least squares method or the M estimation method in the processing of step S3030 illustrated in FIG. 17. However, the normal structure estimation method is not limited to the above-described methods. For example, the normal structure estimation unit 2520 can obtain a conversion matrix that maximizes an evaluation reference that is the number of points (inliers) where the difference $\epsilon i$ of the formula (1) is equal to or less than a predetermined threshold.

Further, the detected boundary 1005 of the retinal pigment epithelium and all points of the normal state data are used in the normal structure estimation processing performed in step S3030 illustrated in FIG. 17. However, the number of points to be used in the above-described processing can be reduced by thinning out some points at appropriate intervals. Further, any conventional method can be used to realize the application processing between groups of three-dimensional points.

Further, the normal structure estimation unit 2520 can classify the boundary 1005 of the retinal pigment epithelium, which has been detected from the present tomographic image, into a normal range and an abnormal range and then perform the above-described application processing on only the normal range of the boundary 1005 of the retinal pigment epithelium. In this case, the normal structure estimation unit 2520 can perform the abnormal range detection, for example, based on a local curvature of the boundary 1005 of the retinal pigment epithelium. More specifically, the normal structure estimation unit 2520 calculates a local curvature of the boundary 1005 of the retinal pigment epithelium and identifies portions where the change rate of the curvature is equal to or greater than a threshold and a region connecting these portions as an abnormal range.

The coordinate conversion applied to the normal state data is not limited to the uniform conversion expressed by the formula (1) that is applied to the entire shape. For example, a conversion accompanied by a local deformation in shape can be allowed. For example, it is useful to apply a penalty term to a shape that is different from the normal state data (in other words, it is useful to permit a shape that is different from the normal state data in a certain range) and perform free-form deformation based application processing.

A second modified example of the present exemplary embodiment is described below. In the above-described exemplary embodiments, an assembly of three-dimensional coordinates that represent the boundary is used to express the normal state data representing the boundary of the retinal pigment epithelium. However, the normal state data description method is not limited to the above-described method. For example, z-coordinate values of the boundary at some sampling points on the x-y plane can be stored as normal state data.

Further, it is useful to employ an appropriate function capable of expressing a plane to approximate the assembly of three-dimensional coordinates and store parameters of the function as normal state data. In this case, it is useful to generate the assembly of three-dimensional coordinates that represent normal state data by inputting each coordinate data on the x-y plane to the function before performing the normal state data application processing in step S3030 illustrated in FIG. 17. Alternatively, any other conventional method for estimating coordinate conversion for applying a group of points to a function can be used to perform the above-described application processing.

A third modified example of the present exemplary embodiment is described below. In the above-described exemplary embodiments, in step S2040 illustrated in FIG. 16, the instruction whether to store the detected boundary 1005 of the retinal pigment epithelium as its normal state data is acquired from an external source. Then, according to this instruction, the detection result is stored as normal state data of the object (i.e., the eye to be inspected).

However, the method for determining whether to store the detection result as normal state data is not limited to the above-described method. For example, in a case where normal state data of the object (i.e., the eye to be inspected) is not yet registered in the data server 130, it is useful to unconditionally store a detection result as normal state data irrespective of the presence of such an instruction. It is also useful to constantly store a latest detection result as normal state data regardless of the presence of normal state data of the object (i.e., the eye to be inspected) registered in the data server 130.

Further, it is useful to store a plurality of normal state data having been previously registered in association with their shooting date and time information and generate normal state data corresponding to designated date and time from the stored information. Further, for example, it is useful to perform three-dimensional alignment processing on normal state data and generate normal state data by performing extrapolation processing based on shooting date and time and usage date and time.

A fourth modified example of the present exemplary embodiment is described below. In the above-described exemplary embodiments, the initial alignment between a tomographic image and normal state data is performed using the fovea centralis of the macula lutea portion. However, any other method can be used to perform the initial alignment. For example, it is useful to obtain centroids of the detected boundary 1005 of the retinal pigment epithelium and the normal state data and then perform rough alignment so that their centroids can coincide with each other.

A fifth modified example of the present exemplary embodiment is described below. In the above-described exemplary embodiments, the analysis processing is performed on the entire region of the acquired three-dimensional tomographic image. However, it is also useful to select a target cross section from the three-dimensional tomographic image and perform processing on a selected two-dimensional tomographic image. For example, it is also useful to perform processing on a cross section that includes a specific portion of a predetermined eyeground (e.g., fovea centralis). In this case, each of the detected layer boundary, the normal structure, and the normal state data is two-dimensional data on the processed cross section. Then, as the conversion matrix A in the processing of step S3030 illustrated in FIG. 17, it is useful to estimate a 3×3 matrix that represents a two-dimensional rigid conversion in the cross section.

A sixth modified example of the present exemplary embodiment is described below. In the above-described exemplary embodiments, the turbulence in the shape of the retinal pigment epithelium is quantified by detecting a boundary between the retinal pigment epithelium 1001 and the layer located beneath the retinal pigment epithelium 1001 and estimating a normal structure of the detected boundary. However, it is also useful to detect a boundary between the retinal pigment epithelium 1001 and the layer located above the retinal pigment epithelium 1001 and estimating a normal structure of the detected boundary.

Further, the entire region of the retinal pigment epithelium 1001 can be regarded as an object to be processed. Further, the layer to be used to quantify the turbulence in shape is not limited to the retinal pigment epithelium 1001. A peripheral layer whose behavior is similar to a disease can be regarded as an object to be processed. More specifically, it is useful to detect any other layer or its boundary if it changes into a wavy shape due to a disease (e.g., age-related macular degeneration) and estimate a normal structure and quantify the turbulence in shape.

A seventh modified example of the present exemplary embodiment is described below. In the above-described exemplary embodiments, normal state data of the object (i.e., the eye to be inspected) having been previously measured is used to estimate a normal structure in a case where the boundary 1005 of the retinal pigment epithelium has deformed due to a disease. However, in a case where at least a part of the boundary 1005 of the retinal pigment epithelium cannot be explicitly observed (i.e., no image features can be obtained) on the tomographic image due to the influence of a blood vessel or a facula, it is useful to use the normal state data of the object (i.e., the eye to be inspected) for the purpose of assisting the detection.

For example, it is now assumed that the boundary 1005 of the retinal pigment epithelium detected by the layer detection unit 2510 has a missing part. In this case, estimation of a layer boundary that corresponds to the missing part is feasible by performing the normal state data application processing (see step S3030 in FIG. 17) on the boundary 1005 of the retinal pigment epithelium that includes the missing part.

Alternatively, the normal state data application processing on the tomographic image can realize the processing itself for detecting the boundary 1005 of the retinal pigment epithelium to be performed by the layer detection unit 2510. Further, it is useful to perform the processing for detecting the boundary 1005 of the retinal pigment epithelium considering such a constraint condition that the boundary 1005 of the retinal pigment epithelium and the normal state data are similar in shape. For example, it is useful to perform detection processing based on the dynamic contour method by applying a penalty term to a shape of the detected boundary 1005 of the retinal pigment epithelium that is different from the normal state data.

An eighth modified example of the present exemplary embodiment is described below. In the above-described exemplary embodiments, the tomographic image capturing apparatus 120 may not be connected to the image processing apparatus 110. For example, in a case where a tomographic image (i.e., a processing target) is already stored in the data server 130 as previously captured image data, it is useful to read out the stored image data and process the readout data. In this case, the image acquisition unit 2200 requests the data server 130 to transmit the tomographic image of the object (i.e., the eye to be inspected) and acquires the tomographic image transmitted from the data server 130. Then, the layer detection unit 2510 detects a layer boundary and the quantification unit 2530 performs quantification processing.

On the other hand, the data server 130 may not be connected to the image processing apparatus 110 if the external storage device 114 performs the role of the image processing apparatus 110.

To realize the above-described constituent components illustrated in FIG. 14 and FIG. 18, which constitute the image processing apparatus 110 according to the exemplary embodiments of the present invention, and the steps of the flowcharts illustrated in FIG. 15 to FIG. 17 and FIG. 19, the CPU (111) can execute a program stored in an external storage device. The present invention encompasses the above-described program and a computer-readable storage medium that stores the program.

Further, the present invention can be embodied, for example, as a system, an apparatus, a method, a program, or a recording medium. More specifically, the present invention can be applied to a system that includes a plurality of devices and can be also applied to an apparatus configured as a single device.

The present invention encompasses supplying directly, or from a remote place, a software program that can realize the functions described in respective exemplary embodiments (i.e., the programs corresponding to the flowcharts illustrated in FIGS. 15 to 17 and 19 in the exemplary embodiments) to a system or an apparatus. Then, a computer installed on the system or the apparatus can read out a supplied program code and executes the readout program to attain the functions of the present invention.

Accordingly, a program code itself to be installed on the computer to cause the computer to realize the functional processing of the present invention can realize the present invention. More specifically, the present invention encompasses the computer program itself that can realize the functional processing of the present invention.

In this case, equivalents of programs (e.g., object code, interpreter program, and OS script data) are usable if they possess comparable functions.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Applications No. 2009-048514 filed Mar. 2, 2009 and No. 2009-048520 filed Mar. 2, 2009, which are hereby incorporated by reference herein in their entirety.

What is claimed is:

1. An image processing apparatus, comprising:
at least one processor that acquires a tomographic image of an eye portion; and
at least one memory to store the tomographic image of the eye portion;
wherein the processor is configured to:
detect a layer of the eye portion from the tomographic image stored in the memory,
detect, in the detected layer, a portion of the detected layer located deeper than a threshold in the depth direction of the eye portion,
calculate, as a normal structure of the detected layer, a curve which does not extend across the detected layer and contacts with a part of the detected layer at the portion of the detected layer, such that the detected layer does not protrude below the calculated curve, and
quantify a difference between the detected layer and the calculated curve,
wherein the normal structure represents a boundary of the retinal pigment epithelium in the depth direction of the eye portion before the boundary is deformed into a wavy shape of the detected layer.

2. The image processing apparatus according to claim 1, wherein
the memory stores the information relating to the wavy shape of the detected layer,
wherein the processor is configured to estimate the normal structure of the layer based on the stored information relating to the wavy shape of the detected layer.

3. The image processing apparatus according to claim 1, wherein the processor is configured to estimate the normal structure of the layer using a mathematical function based on information relating to the wavy shape of the detected layer.

4. The image processing apparatus according to claim 3, wherein the mathematical function is variable depending on a surface portion or the detected portion located deeper than the threshold.

5. The image processing apparatus according to claim 1, wherein the processor is configured to estimate the normal structure of the layer by assuming that a shape of the detected layer is a mixed distribution composed of a mathematical function representing a normal structure and a mathematical function representing the wavy shape.

6. The image processing apparatus according to claim 1, wherein the processor is configured to determine a normal range of the detected layer, and estimate the normal structure of the detected layer based on the normal range.

7. The image processing apparatus according to claim 1, further comprising:
a display device, wherein the processor is further configured to:
cause the display device to display a display form indicating a result of quantification of the difference between the detected layer and the calculated curve.

8. The image processing apparatus according to claim 7, wherein the processor is configured to quantify the state of the layer according to a feature that reflects a difference between the normal structure estimated and a structure of the detected layer.

9. The image processing apparatus according to claim 8, wherein the feature that reflects the difference is based on either one of thickness, area, volume, and density of the layer.

10. The image processing apparatus according to claim 1, wherein the processor acquires the tomographic image of an eyeground of the eye portion, and
wherein the processor detects from the tomographic image the layer of the eyeground.

11. The image processing apparatus according to claim 7, wherein the processor compares the result of quantification with past quantification data and causes the display device to display the comparison.

12. The image processing apparatus according to claim 7, wherein the processor superimposes a difference area indicating a difference between the detected layer and the normal structure on the tomographic image and causes the display device to display the superimposed image.

13. The image processing apparatus according to claim 7, wherein the processor superimposes the display form indicating the normal structure on the tomographic image and causes the display device to display the superimposed image.

14. The image processing apparatus according to claim 1, wherein the processor estimates, as the normal structure, a boundary of the detected layer before deformation of the boundary into the wavy shape.

15. The image processing apparatus according to claim 1,
wherein the processor is further configured to set, in the tomographic image, the threshold with respect to the depth direction of the eye portion.

16. A method accomplished by an image processing apparatus having at least one processor and at least one memory, the method comprising:
acquiring a tomographic image of an eye portion;
storing the tomographic image of the eye portion in the memory;
detecting, with the processor, a layer of the eye portion from the tomographic image stored in the memory;
detecting, with the processor, in the detected layer, a portion of the detected layer located deeper than a threshold in the depth direction of the eye portion,
calculating, with the processor, as a normal structure of the detected layer, a curve which does not extend across the detected layer and contacts with a part of the detected layer at the portion of the detected layer, such that the detected layer does not protrude below the calculated curve; and
quantifying a difference between the detected layer and the calculated curve,
wherein the normal structure represents of a boundary of the retinal pigment epithelium in the depth direction of the eye portion before the boundary is deformed into a wavy shape of the detected layer.

17. The method according to claim 16, wherein estimating the normal structure includes estimating, with the processor, a boundary of the detected layer before deformation of the boundary into the wavy shape.

18. A non-transitory computer-readable medium storing a program that when executed by at least one processor performs a method for controlling an image processing apparatus, comprising:
computer-executable instructions for acquiring a tomographic image of an eye portion;
computer-executable instructions for storing the tomographic image of the eye portion in at least one memory;
computer-executable instructions for detecting a layer of the eye portion from the tomographic image stored in the memory;
computer-executable instructions for detecting, in the detected layer, a portion of the detected layer located deeper than a threshold in the depth direction of the eye portion,
computer-executable instructions for calculating, as a normal structure of the detected layer, a curve which does not extend across the detected layer and contacts with a part of the detected layer at the portion of the detected layer, such that the detected layer does not protrude below the calculated curve; and
computer-executable instructions for quantifying a difference between the detected layer and the calculated curve,
wherein the normal structure represents a boundary of the retinal pigment epithelium in the depth direction of the eye portion before the boundary is deformed into a wavy shape of the detected layer.

19. An image processing apparatus, comprising:
at least one processor that acquires a tomographic image of an eye portion; and
at least one memory to store the tomographic image of the eye portion,
wherein the processor is configured to:
detect a layer of the eye portion from the tomographic image stored in the memory;
detect, in the detected layer, a portion of the detected layer located deeper than a threshold in the depth direction of the eye portion,
calculate, as a normal structure of the detected layer, a curve which does not extend across the detected layer and contacts with a part of the detected layer at the portion of the detected layer, such that the detected layer does not protrude below the calculated curve, using normal state data of the detected layer; and
quantify a difference between the detected layer and the calculated curve,
wherein the normal structure represents a boundary of the retinal pigment epithelium in the depth direction of the eye portion before the boundary is deformed into a wavy shape of the detected layer.

20. The image processing apparatus according to claim 19, further comprising:
a display device,
wherein the processor is further configured to:
cause the display device to display a display form indicating a result of quantification of the difference between the detected layer and the calculated curve.

21. The image processing apparatus according to claim 20, wherein the processor compares the result of quantification with past quantification data and causes the display device to display the comparison.

22. The image processing apparatus according to claim 20, wherein the processor superimposes a difference area indicating a difference between the detected layer and the normal structure on the tomographic image and causes the display device to display the superimposed image.

23. The image processing apparatus according to claim 20, wherein the processor superimposes a display form indicating the normal structure on the tomographic image and causes the display device to display the superimposed image.

24. The image processing apparatus according to claim 20, wherein the processor is further configured to:
to determine whether a state of the detected layer is normal or not normal based on a detection result of the detected layer,
wherein the processor estimates the normal structure of the detected layer in a case where the processor determines that the state of the detected layer is not normal.

25. The image processing apparatus according to claim 24,
wherein the processor is further configured to:
acquire an instruction whether to store in the memory the detection result of the detected layer as the normal state data or not, and
output the detection result of the detected layer as the normal state data in a case where the processor determines that the state of the detected layer is normal and acquires the instruction to store the detection result.

26. The image processing apparatus according to claim 19,
wherein the detected layer is a retinal pigment epithelium of an eyeground of the eye portion.

27. The image processing apparatus according to claim 19, wherein the processor estimates, as the normal structure, a boundary of the detected layer before deformation of the boundary into the wavy shape.

28. An image processing apparatus comprising:
at least one processor configured to:
detect a layer from a tomographic image of an eyeground of an eye portion;
detect, in the detected layer, a portion of the detected layer located deeper than a threshold in the depth direction of the eye portion,
calculate, as a normal structure of the detected layer, a convex curve in the depth direction of the eyeground of the eye based on a shape of the detected layer such that the convex curve does not extend across the detected layer and contacts with a part of the detected layer at the portion of the detected layer, such that the detected layer does not protrude below the calculated convex curve; and
quantify a difference between the detected layer and the convex curve,
wherein the normal structure represents a boundary of the retinal pigment epithelium in the depth direction of the eye portion before the shape of the detected layer is deformed into a wavy shape.

29. The image processing apparatus according to claim 28, wherein the processor is further configured to:
detect a plurality of features of the detected layer based on a shape of the detected layer,
wherein the processor calculates the convex curve based on the plurality of features.

30. The image processing apparatus according to claim 29,
wherein the processor detects a deep portion in a deep place of the detected layer in the depth direction, and
wherein the processor calculates the convex curve based on the plurality of features including the deep portion.

31. The image processing apparatus according to claim 29, wherein the processor calculates a quadratic curve based on the plurality of features as the curve.

32. The image processing apparatus according to claim 31, wherein the processor calculates the quadratic curve with a smallest difference from the detected layer by applying the method of least squares.

33. The image processing apparatus according to claim 29, wherein the processor applies a function to each of the plurality of features, changes a weight of the function according to a sign of a difference between the plurality of features and the function, and estimates the curve as the normal structure of the layer.

34. The image processing apparatus according to claim 29,
wherein the processor detects a group of coordinate points representing a boundary of the detected layer as the plurality of features, and
wherein the processor applies a quadratic function to the group of coordinate functions and estimates the curve as the normal structure of the detected layer.

35. The image processing apparatus according to claim 28, further comprising:
a display device,
wherein the processor causes the display device to display a display form indicating a result of quantification by the quantification unit.

36. The image processing apparatus according to claim 35, wherein the processor compares the result of quantification with past quantification data and causes the display device to display the comparison.

37. The image processing apparatus according to claim 35, wherein the processor superimposes a difference area indicating a difference between the detected layer and the curve on the tomographic image and causes the display device to display the superimposed image.

38. The image processing apparatus according to claim 35, wherein the processor superimposes a display form indicating the normal structure on the tomographic image and causes the display device to display the superimposed image.

39. The image processing apparatus according to claim 38, wherein the result of quantification by the processor is at least one of a distance between the detected layer and the curve, an area, and a volume.

40. The image processing apparatus according to claim 28, wherein the processor calculates the curve for each of a plurality of two-dimensional tomographic images of a three-dimensional tomographic image of the eyeground.

41. The image processing apparatus according to claim 28, wherein the processor detects a layer corresponding to the retinal pigment epithelium of the eyeground in the tomographic image.

42. The image processing apparatus according to claim 28, wherein the processor detects an edge component from the tomographic image as the boundary of the layer.

43. A method accomplished by an image processing apparatus including at least one processor and at least one memory, the method comprising:
detecting, with the processor, a layer of an eye portion from a tomographic image of an eyeground portion of an eye;
detecting, with the processor, in the detected layer, a portion of the detected layer located deeper than a threshold in the depth direction of the eye portion,
calculating, with the processor, as a normal structure of the detected layer, a convex curve of the detected layer in the depth direction of the eyeground of the eye portion based on a shape of the detected layer such that the convex curve does not extend across the detected layer and contacts with a part of the detected layer at the portion of the detected layer, such that the detected layer does not protrude below the calculated curve; and quantifying a difference between the detected layer and the convex curve, wherein the normal structure represents a boundary of the retinal pigment epithelium in the depth direction of the eye portion before the shape of the detected layer is deformed into a wavy shape.

44. A non-transitory computer-readable medium storing a program that causes a computer to execute steps of the method for processing an image according to claim 43.

45. A method accomplished by an image processing apparatus including at least one processor and at least one memory, the method comprising:

acquiring a tomographic image of an eye portion;

storing the tomographic image of the eye portion in the memory;

detecting, with the processor, a layer of the eye portion from the tomographic image stored in the memory;

detecting, with the processor, in the detected layer, a portion of the detected layer located deeper than a threshold in the depth direction of the eye portion, calculating, with the processor, as a normal structure of the detected layer, a curve which does not extend across the detected layer and contacts with a part of the detected layer at the portion of the detected layer, such that the detected layer does not protrude below the calculated curve, using normal state data of the detected layer; and quantifying a difference between the detected layer and the calculated curve, wherein the normal structure represents a boundary of the retinal pigment epithelium in the depth direction of the eye portion before the boundary is deformed into a wavy shape of the detected layer.

46. A non-transitory computer-readable medium storing a program that causes a computer to execute steps of the method for processing an image according to claim 45.

47. The method according to claim 45, wherein estimating the normal structure includes estimating, with the processor, a boundary of the detected layer before deformation of the boundary into the wavy shape.

48. An image processing apparatus comprising:

at least one memory that stores a plurality of tomographic images that each depicts layer structures of a fundus of an eye; and at least one processor that, based on pixel values of pixels of each of said stored tomographic images, identifies a layer region in a tomographic image that corresponds to a pigment layer of a retina of the eye, wherein the processor is configured to detect, in the identified layer region, a portion of the identified layer region located deeper than a threshold in the depth direction of the retina of the eye, wherein, the processor, based on a shape of said identified layer region, calculates a convex curve in a direction of depth of said fundus such that the convex curve does not extend across the identified layer region and contacts with a part of the identified layer region at the portion of the detected layer, such that the detected layer does not protrude below the calculated convex curve; and wherein, the processor, based on said identified layer region and the convex curve, identifies difference regions that quantify the identified layer region and the convex curve.

49. An image processing apparatus according to claim 48, wherein the processor, that obtains the convex curve, further identifies a plurality of characteristic regions within said layer region based on the shape of the identified layer region, and obtains said curve based on the identified plurality of characteristic regions.

50. The image processing apparatus according to claim 49, wherein the processor, that obtains the convex curve, obtains a quadratic curve based on the identified plurality of characteristic regions as said curve.

51. The image processing apparatus according to claim 48, wherein the processor generates morphological information representing morphology of the identified difference regions.

52. An image processing apparatus comprising:

at least one memory that stores three-dimensional images depicting layer structures of a fundus of an eye; and at least one processor that, based on pixel values of pixels of said stored three-dimensional images, identifies a layer region in a three-dimensional image that corresponds to a pigment layer of a retina of the eye;

wherein the processor is configured to detect, in the identified layer region, a portion of the identified layer region located deeper than a threshold in the depth direction of the retina of the eye, wherein, the processor, based on a shape of said identified layer region, calculates a convex curved surface in the direction of depth of said fundus such that the convex curved surface does not extend across the identified layer region and contacts with a part of the identified layer region at the portion of the identified layer region, such that the identified layer region does not protrude below the calculated convex curve, and wherein, the processor, based on said identified layer region and the convex curved surface, identifies difference regions that quantify the identified layer region and the convex curved surface.

53. The image processing apparatus according to claim 52, wherein the processor generates morphological information representing morphology of the identified difference regions.

54. An image processing method to processes a plurality of tomographic images that each depicts layer structures of a fundus of an eye, comprising the steps of:

for each of said plurality of tomographic images, identifying with at least one processor a layer region in a tomographic image that corresponds to a pigment layer of a retina of the eye based on pixel values of pixels of the tomographic image;

detecting, in the identified layer region, a portion of the identified layer region located deeper than a threshold in the depth direction of the retina, calculating, with the processor, based on a shape of said identified layer region, a convex curve in the direction of depth of said fundus such that the convex curve does not extend across the identified layer region and contacts with a part of the identified layer region at the portion of the identified layer region, such that the identified layer region does not protrude below the calculated convex curve; and identifying, with the processor, based on said identified layer region and the convex curve, difference regions that quantify the identified layer region and the convex curve.

55. A non-transitory computer-readable medium storing a program that causes a computer to execute the steps of the image processing method according to claim 54.

56. An image processing method to processes three-dimensional images depicting layer structures of a fundus of an eye, comprising the steps of:
   identifying with at least one processor, based on pixel values of pixels of said three-dimensional image, a layer region in a three-dimensional image that corresponds to a pigment layer of the retina of the eye;
   detecting with the processor, in the identified layer region, a portion of the identified layer region located deeper than a threshold in the depth direction of the retina,
   calculating, with the processor, based on a shape of said identified layer region, a convex curved surface in a direction of depth of said fundus such that the convex curved surface does not extend across the identified layer region and contacts with a part of the identified layer region at the portion of the identified layer region, such that the identified layer region does not protrude below the calculated convex curve; and
   identifying, with the processor, based on said identified layer region and the convex curved surface, difference regions that quantify the identified layer region and the convex curved surface.

57. A non-transitory computer-readable medium storing a program that causes a computer to execute the steps of the image processing method according to claim 56.

* * * * *